(12) United States Patent
Held

(10) Patent No.: US 11,299,731 B1
(45) Date of Patent: Apr. 12, 2022

(54) CRISPR EDITING TO EMBED NUCLEIC ACID LANDING PADS INTO GENOMES OF LIVE CELLS

(71) Applicant: Inscripta, Inc., Boulder, CO (US)

(72) Inventor: Daniel Held, Boulder, CO (US)

(73) Assignee: Inscripta, Inc., Boulder, CO (US)

( * ) Notice: Subject to any disclaimer, the term of this patent is extended or adjusted under 35 U.S.C. 154(b) by 0 days.

(21) Appl. No.: 17/475,267

(22) Filed: Sep. 14, 2021

Related U.S. Application Data

(60) Provisional application No. 63/078,789, filed on Sep. 15, 2020.

(51) Int. Cl.
| | | |
|---|---|---|
| C12N 15/10 | (2006.01) | |
| C12N 15/63 | (2006.01) | |
| C12N 15/11 | (2006.01) | |

(52) U.S. Cl.
CPC ..... *C12N 15/1093* (2013.01); *C12N 15/1082* (2013.01); *C12N 15/111* (2013.01); *C12N 15/63* (2013.01); *C12N 2310/20* (2017.05)

(58) Field of Classification Search
None
See application file for complete search history.

(56) References Cited

U.S. PATENT DOCUMENTS

| | | |
|---|---|---|
| 6,391,582 B2 | 5/2002 | Ying et al. |
| 6,837,995 B1 | 1/2005 | Vassarotti et al. |
| 7,166,443 B2 | 1/2007 | Walker et al. |
| 8,332,160 B1 | 12/2012 | Platt et al. |
| 8,697,359 B1 | 4/2014 | Zhang et al. |
| 8,926,977 B2 | 1/2015 | Miller et al. |
| 9,260,505 B2 | 2/2016 | Weir et al. |
| 9,361,427 B2 | 6/2016 | Hillson |
| 9,499,855 B2 | 11/2016 | Hyde et al. |
| 9,776,138 B2 | 10/2017 | Innings et al. |
| 9,790,490 B2 | 10/2017 | Zhang et al. |
| 9,896,696 B2 | 2/2018 | Begemann et al. |
| 9,982,279 B1 | 5/2018 | Gill et al. |
| 9,988,624 B2 | 6/2018 | Serber et al. |
| 10,011,849 B1 | 7/2018 | Gill et al. |
| 10,017,760 B2 | 7/2018 | Gill et al. |
| 10,227,576 B1 | 3/2019 | Cameron et al. |
| 10,266,851 B2 | 4/2019 | Chen |

(Continued)

FOREIGN PATENT DOCUMENTS

| | | |
|---|---|---|
| EP | 2395087 | 12/2011 |
| EP | 3199632 | 8/2017 |

(Continued)

OTHER PUBLICATIONS

International Search Report and Written Opinion for International Application No. PCT/US20/19379, dated Jul. 22, 2020, p. 1-10.

(Continued)

*Primary Examiner* — Kaijiang Zhang
(74) *Attorney, Agent, or Firm* — Sarah Brashears

(57) ABSTRACT

The present disclosure relates to compositions, methods, modules and automated integrated instrumentation for multiplex delivery of "landing pad" edits into the genomes of a population of live cells. The landing pads then may be leveraged to insert very large DNA sequences into the genomes of the population of live cells.

30 Claims, 12 Drawing Sheets

Specification includes a Sequence Listing.

LANDING PAD EDIT WORKFLOW

(56) References Cited

U.S. PATENT DOCUMENTS

| | | |
|---|---|---|
| 10,704,033 B1 | 7/2020 | Kim et al. |
| 10,724,021 B1 | 7/2020 | Kim et al. |
| 10,745,678 B1 | 8/2020 | Kim et al. |
| 10,767,169 B1 | 9/2020 | Kim et al. |
| 10,837,021 B1 | 11/2020 | Tian et al. |
| 10,927,385 B2 | 2/2021 | Kannan et al. |
| 2002/0139741 A1 | 10/2002 | Kopf |
| 2004/0110253 A1 | 6/2004 | Kappler et al. |
| 2006/0014137 A1 | 1/2006 | Ghosh et al. |
| 2007/0020761 A1 | 1/2007 | Yu et al. |
| 2010/0076057 A1 | 3/2010 | Sontheimer et al. |
| 2011/0294217 A1 | 12/2011 | McConnell-Smith et al. |
| 2013/0236970 A1 | 9/2013 | Anneren et al. |
| 2014/0068797 A1 | 3/2014 | Doudna et al. |
| 2014/0199767 A1 | 7/2014 | Barrangou et al. |
| 2014/0242033 A1 | 8/2014 | Gruber et al. |
| 2014/0273226 A1 | 9/2014 | Wu et al. |
| 2015/0024464 A1 | 1/2015 | Lippow et al. |
| 2015/0071898 A1 | 3/2015 | Liu et al. |
| 2015/0098954 A1 | 4/2015 | Hyde et al. |
| 2015/0159174 A1 | 6/2015 | Frendewey et al. |
| 2015/0176013 A1 | 6/2015 | Musunuru et al. |
| 2015/0191719 A1 | 7/2015 | Hudson et al. |
| 2015/0225732 A1 | 8/2015 | Williams et al. |
| 2015/0344549 A1 | 12/2015 | Muir et al. |
| 2016/0024529 A1 | 1/2016 | Carstens et al. |
| 2016/0053272 A1 | 2/2016 | Wurzel et al. |
| 2016/0053304 A1 | 2/2016 | Wurzel et al. |
| 2016/0076093 A1 | 3/2016 | Shendure et al. |
| 2016/0102322 A1 | 4/2016 | Ravinder et al. |
| 2016/0130608 A1 | 5/2016 | Doudna et al. |
| 2016/0168592 A1 | 6/2016 | Church et al. |
| 2016/0264981 A1 | 9/2016 | Yang et al. |
| 2016/0281053 A1 | 9/2016 | Sorek et al. |
| 2016/0289673 A1 | 10/2016 | Huang et al. |
| 2016/0298134 A1 | 10/2016 | Chen et al. |
| 2016/0354487 A1 | 12/2016 | Zhang et al. |
| 2017/0002339 A1 | 1/2017 | Barrngou et al. |
| 2017/0022499 A1 | 1/2017 | Lu et al. |
| 2017/0044525 A1 | 2/2017 | Kaper et al. |
| 2017/0051310 A1 | 2/2017 | Doudna et al. |
| 2017/0073705 A1 | 3/2017 | Chen et al. |
| 2017/0191123 A1 | 7/2017 | Kim et al. |
| 2017/0211078 A1 | 7/2017 | Kamineni et al. |
| 2017/0240922 A1 | 8/2017 | Gill et al. |
| 2017/0369870 A1 | 12/2017 | Gill et al. |
| 2018/0028567 A1 | 2/2018 | Li et al. |
| 2018/0052176 A1 | 2/2018 | Holt et al. |
| 2018/0073013 A1 | 3/2018 | Lorenz et al. |
| 2018/0112235 A1 | 4/2018 | Li et al. |
| 2018/0187149 A1 | 7/2018 | Ma et al. |
| 2018/0200342 A1 | 7/2018 | Bikard et al. |
| 2018/0230460 A1 | 8/2018 | Gill et al. |
| 2018/0230461 A1 | 8/2018 | Gill et al. |
| 2018/0284125 A1 | 10/2018 | Gordon et al. |
| 2019/0017072 A1 | 1/2019 | Ditommaso et al. |
| 2019/0085324 A1 | 3/2019 | Regev et al. |
| 2019/0136230 A1 | 5/2019 | Sather et al. |
| 2019/0169605 A1 | 6/2019 | Masquelier et al. |
| 2019/0194650 A1* | 6/2019 | Gill et al. .......... C12N 15/1065 |
| 2019/0225928 A1 | 7/2019 | Masquelier et al. |
| 2019/0270987 A1 | 9/2019 | Masquelier et al. |
| 2020/0071660 A1* | 3/2020 | Spindler et al. ....... G01N 35/10 |
| 2020/0095533 A1 | 3/2020 | Garst et al. |
| 2020/0216794 A1 | 7/2020 | Belgrader et al. |
| 2020/0263197 A1 | 8/2020 | Cheng et al. |
| 2020/0270632 A1* | 8/2020 | Roy et al. .............. C12N 15/11 |

FOREIGN PATENT DOCUMENTS

| | | |
|---|---|---|
| WO | WO2002/010183 | 2/2002 |
| WO | WO 2003/087341 | 10/2003 |
| WO | WO 2010/079430 | 7/2010 |
| WO | WO 2011/072246 | 6/2011 |
| WO | WO 2011/143124 | 11/2011 |
| WO | WO 2013/142578 | 9/2013 |
| WO | WO 2013/176772 | 11/2013 |
| WO | WO 2014/018423 | 1/2014 |
| WO | WO2014/143381 | 9/2014 |
| WO | WO 2014/144495 | 9/2014 |
| WO | WO2016/110453 | 7/2016 |
| WO | WO 2016/110453 | 7/2016 |
| WO | WO 2017/053902 | 3/2017 |
| WO | WO2017/075265 | 5/2017 |
| WO | WO 2017/078631 | 5/2017 |
| WO | WO 2017/083722 | 5/2017 |
| WO | WO2017/106414 | 6/2017 |
| WO | WO 2017/106414 | 6/2017 |
| WO | WO 2017/161371 | 9/2017 |
| WO | WO 2017/174329 | 10/2017 |
| WO | WO 2017/186718 | 11/2017 |
| WO | WO2017/212400 | 12/2017 |
| WO | WO 2017/216392 | 12/2017 |
| WO | WO2017/216392 | 12/2017 |
| WO | WO2017/223330 | 12/2017 |
| WO | WO 2017/223330 | 12/2017 |
| WO | WO 2018/031950 | 2/2018 |
| WO | WO 2018/071672 | 4/2018 |
| WO | WO 2018/083339 | 5/2018 |
| WO | WO 2018/152325 | 8/2018 |
| WO | WO2018/152325 | 8/2018 |
| WO | WO2018/172556 | 9/2018 |
| WO | WO 2018/191715 | 10/2018 |
| WO | WO2019/006436 | 1/2019 |
| WO | WO2019/055878 | 3/2019 |
| WO | WO2019/200004 | 10/2019 |
| WO | WO2019/209926 | 10/2019 |
| WO | WO2020/005383 | 1/2020 |
| WO | WO2020/021045 | 1/2020 |
| WO | WO2020/074906 | 4/2020 |

OTHER PUBLICATIONS

International Search Report and Written Opinion for International Application No. PCT/US20/36064, dated Sep. 18, 2020, p. 1-16.
International Search Report and Written Opinion for International Application No. PCT/US20/40389, dated Oct. 13, 2020, p. 1-12.
Arnak, et al., "Yeast Artificial Chromosomes", John Wiley & Sons, Ltd., doi:10.1002/9780470015902.a0000379.pub3, pp. 1-10 (2012).
Woo, et al., "Dual roles of yeast Rad51 N-terminal domain in repairing DNA double-strand breaks", Nucleic Acids Research, doi:10.1093/nar/gkaa.587, vol. 48, No. 15, pp. 8474-8489 (2020).
International Search Report and Written Opinion for International Application No. PCT/US2021/012868, dated Mar. 26, 2021, p. 1-15.
Anzalone et al., "Search-and-replace genome editing without doubles-strand breaks or donor DNA," Nature, Oct. 21, 2019, vol. 576, No. 7785, pp. 149-157.
Alvarez, et al., "In vivo diversification of target genomic sites using processive T7 RNA polymerase-base deaminase fusions blocked by RNA-guided dCas9", Dept.of Microbial Biotechnology and Systems Biology Program, Madrid, Spain, Jan. 1, 2019, p. 1-33.
International Search Report and Written Opinion for International Application No. PCT/US20/65168, dated Mar. 17, 2021, p. 1-15.
International Search Report and Written Opinion for International Application No. PCT/US2020/038345, dated Nov. 23, 2020, p. 1-13.
International Search Report and Written Opinion for International Application No. PCT/US21/12867, dated May 12, 2021, p. 1-17.
International Search Report and Written Opinion for International Application No. PCT/US2020/064727, dated Apr. 28, 2021, p. 1-13.
International Search Report and Written Opinion for International Application No. PCT/US21/29008, dated Aug. 24, 2021, p. 1-19.
International Search Report and Written Opinion for International Application No. PCT/US21/29011, dated Aug. 24, 2021, p. 1-20.
Bauer, et al., "Cell-microcarrier Adhesion to Gas-Liquid Interfaces and Foam", Biotechnol. Prog. 2000, 16, 125-132, Oct. 19, 1999.
Datlinger, et al., "Pooled CRISPR screening with single-cell transcriptome readout", Nature Methods, Jan. 10, 2017; p. 1-10, doi:10.1038/nmeth.4177.

(56) References Cited

OTHER PUBLICATIONS

Dixit, et al., "Perturb-Seq: Dissecting Molecular Circuits with Scalable Single-Cell RNA Profiling of Pooled Genetic Screens", Cell 167, p. 1853-1866, Dec. 15, 2016.
GE Healthcare Life Sciences, "Microcarrier Cell Culture Principles and Methods", 18-1140-62 AC, p. 1-23, Nov. 2013.
Jacobi, et al., "Simplified CRISPR tools for efficient genome editing and streamlined protocols for their delivery into mammalian cells and mouse zygotes", Methods 121-122, p. 16-28, Mar. 23, 2017.
Jaitin, et al., "Dissecting Immune Circuits by Linking CRISPR-Pooled Screens with Single-Cell RNA-Seq", Cell 167, p. 1883-1896, Dec. 15, 2016.
Kim, et al., "Formation of Thermoresponsive Poly(N-isopropylacrylamide)/Dextran Particles by Atom Transfer Radical Polymerization", Macromol. Rapid Commun., 24, p. 517-521, 2003.
Kimple, et al., "Overview of Affinity Tags for Protein Purification", Curr Protoc Protein Sci.; 73: Unit-9-9. Doi:10.1002/0471140864. ps0909s73, p. 1-26, Aug. 6, 2015.
Nienow, et al., "A potentially scalable method for the harvesting of hMSCs from microcarriers", Biochemical Engineering Journal 85, p. 79-88, Feb. 4, 2014.
Replogle, et al., "Direct capture of CRISPR guides enables scalable, multiplexed, and multi-omic Perturb-Seg", bioRxiv; doi:http://dx.doi.org/10.1101/503367, p. 1-26, Dec. 21, 2018.
Sivalingam, et al., "Superior Red Blood Cell Generation from Human Pluripotent Stem Cells Through a Novel Microcarrier-Based Embryoid Body Platform", Tissue Engineering: Part C, vol. 22, No. 8, p. 765-780, Jun. 9, 2016.
International Search Report and Written Opinion for International Application No. PCT/US21/35807, dated Nov. 24, 2021, p. 1-21.
International Search Report and Written Opinion for International Application No. PCT/US21/50338, dated Dec. 10, 2021, p. 1-17.
International Search Report and Written Opinion for International Application No. PCT/US21/43097, dated Nov. 19, 2021, p. 1-12.
International Search Report and Written Opinion for International Application No. PCT/US21/39872, dated Oct. 27, 2021, p. 1-14.
International Search Report and Written Opinion for International Application No. PCT/US21/48566, dated Dec. 10, 2021, p. 1-10.
Filsinger, et al., "Characterizing the portability of RecT-mediated oligonucleotide recombination", bioRxiv, Apr. 15, 2020, doi:org/10.1101/2020.04.14.041095, p. 1-25.
Nelson, et al., "Engineered pegRNAs improve prime editing efficiency", Nature Biotechnology, Jul. 25, 2021, doi.org/10.1038/s41587-021-01039-7, p. 1-14.
Yu, et al., "Improved delivery of Cas9 protein/gRNA complexes using lipofectamine CRISPRMAX", Biotechnol Ltt, Feb. 18, 2016, doi 10.1007/sl0529-016-2064-9, p. 919-929.
Bengali, et al., "Gene Delivery Through Cell Culture Substrate Adsorbed DNA Complexes", Biotechnol Bioeng., May 5, 2005, doi:10.1002/bit.20393, p. 1-23.
Segura, et al., "Substrate-mediated DNA delivery: role of the cationic polymer structure and extent of modification", Journal of Controlled Release, Aug. 9, 2003, doi:10.1016/j.jconrel.2003.08.003, p. 69-84.
Takahashi, et al., "Integration of CpG-free DNA induces de novo methylation of CpG islands in pluripotent stem cells," Science, May 5, 2017, vol. 356, No. 6337, pp. 1-7.
Chen, et al., "Human Pluripotent Stem Cell Culture: Considerations for Maintenance, Expansion, and Therapeutics", Cell Stem Cell, Jan. 2, 2014, doi.org/10.1016/j.stem.2013.12.005, p. 13-26.
Fayazpour, F., "Exploring New Applications For Photophysically Encoded Mircrocarriers", Ghent University Faculty of Pharmaceutical Sciences, Thesis Submission, Sep. 2008, 169 pages.
Chueng, et al., "Unlinking the methylome pattern from nucleotide sequence, revealed by large-scale in vivo genome engineering and methylome editing in medaka fish," PLoS Genetics, Dec. 21, 2017, vol. 13, No. 12, pp. 1-25.

Elvin, et al., "Modified bacteriophage lambda promoter vectors for overproduction of proteins in *Escherichia coli*", Gene, 87, Sep. 15, 1989, p. 123-126.
Segall-Shapiro, et al., "Engineered promoters enable constant gene expression at any copy number in bacteria", Nature Biotechology, vol. 36, No. 4, Mar. 19, 2018, p. 352-363.
Xing, et al., "A CRISPR/Cas9 toolkit for multiplex genome editing in plants", BMC Plant Biology, 2014, p. 1-12.
Sun, et al., "A Single Multiplex crRNA Array for FnCpf1-Mediated Human Genome Editing," Molecular Therapy, Aug. 1, 2018, vol. 26, No. 8, pp. 2070-2076.
Kurata, et al., "Highly multiplexed genome engineering using CRISPR/Cas9 gRNA arrays," PLoS ONE, Sep. 17, 2018, vol. 13, No. 9, pp. 1-17.
Hubmann, et al., "Natural and Modified Promoters for Tailored Metabolic Engineering of the Yeast *Saccharomyces cerevisiae*", Methods in Molecular Biology, vol. 1152, doi10.1007/978-1-4939-0563-8_2, p. 17-42.
Unciti-Broceta, et al., "Combining Nebulization-Mediated Transfection and Polymer Microarrays for the Rapid Determination of Optimal Transfection Substrates", Journal of Combinatorial Chemistry, vol. 10, No. 2, Feb. 5, 2008, p. 179-184.
Fayazpour, et al., "Evaluation of Digitally Encoded Layer-by-layer Coated Microparticles as Cell Carriers", Advanced Functional Materials, Sep. 1, 2008, p. 2716-2723.
UniProtKB/TrEMBL, "A0A1G4WF58_9FIRM", Nov. 22, 2017, rerieved from Internet: https://www.uniprot.org/uniprot/A0A_1G4WF58.txt, pp. 1-3.
Natsume, et al., "Conditional Degrons for Controlling Protein Expression at the Protein Level", Annual Review of Genetics, vol. 51, 2017, doi.org/10.1146/annurev-genet-120116-024656, p. 83-104.
Chen, et al., "Enhancing the copy number of episomal plasmids in *Saccharomyces cerevisiae* for improved protein production", FEMS Yeast Research, Apr. 25, 2012, doi:10.1111/j.1567-1364.2012.00809.x; p. 598-607.
Price, et al., "Expanding and understanding the CRISPR toolbox for Bacillus subtilis with MAD7 and dMAD7", Biotechnology and Bioengineering, Feb. 19, 2020, doi:10.1002/bit.27312 p. 1805-1816.
International Search Report and Written Opinion for International Application No. PCT/US21/43534, dated Nov. 10, 2021, p. 1-16.
International Search Report and Written Opinion for International Application No. PCT/US20/26095, dated Jul. 17, 2020, p. 1-10.
Bao, et al., "Genome-scale engineering of *Saccharomyces cerevisiae* with single-nucleotide precision", Nature Biotechnology, doi:10.1038/nbt.4132, pp. 1-6 (May 7, 2018).
Dicarlo, et al., "Genome engineering in *Saccharomyces cervisiae* using CRISPR-Case systems", Nucleic Acids Research, 41(7):4336-43 (2013).
Garst, et al., "Genome-wide mapping of mutations at single-nucleotide resolution for protein, metabolic and genome engineering", Nature Biotechnology, 35(1):48-59 (2017).
Hsu, et al., "DNA targeting specificity of RNA-guided Cas9 nucleases", Nature Biotechnology, 31(9):827-32 (2013).
Jiang, et al., "RNA-guided editing of bacterial genomes using CRISPR-Cas systems", Nature Biotechnology, 31(3):233-41 (2013).
Jinek, et al., "A Programmable Dual-RNA-Guided DNA Endonuclease in Adaptive Bacterial Immunity", Science, 337:816-20 (2012).
Verwaal, et al., "CRISPR/Cpf1 enables fast and simple genome editing of *Saccharamyces cerevisiae*", Yeast, 35:201-11 (2018).
Lian, et al., "Combinatorial metabolic engineering using an orthogonal tri-functional CRISPR system", Nature Communications, DOI:1038/s41467-017-01695-x/www.nature.com/naturecommunications, pp. 1-9 (2017).
Roy, et cl., "Multiplexed precision genome editing with trackable genomic barcodes in yeast", Nature Biotechnolgy, doi:10.1038/nbt.4137, pp. 1-16 (2018).
Dong, "Establishment of a highly efficient virus-inducible CRISPR/Cas9 system in insect cells," Antiviral Res., 130:50-7(2016).
Epinat et al., "A novel engineered meganuclease induces homologous recombination in eukaryotic cells, e.g., yeast and mammalian cells", Nucleic Acids Research, 31(11): 2952-2962.

(56) References Cited

OTHER PUBLICATIONS

Farasat et al., "A Biophysical Model of CRISPR/Cas9 Activity for Rational Design of Genome Editing and Gene Regulation," PLoS Comput Biol., 29:12(1):e1004724 (2016).
Liu et al., "A chemical-inducible CRISPR-Cas9 system for rapid control of genome editing", Nature Chemical Biology, 12:980-987(2016).
Eklund, et al., "Altered target site specificity variants of the I-Ppol His-Cys bis homing endonuclease" Nucleic Acids Research, 35(17):5839-50 (2007).
Boles, et al., "Digital-to-biological converter for on-demand production of biologies", Nature Biotechnology, doi:10.1038/nbt.3859 (May 29, 2017).
Pines, et al., "Codon Compression Algorithms for Saturation Mutagenesis", ACS Synthetic Biology, 4:604-14 (2015).
Bessa et al., "Improved gap repair cloning in yeast: treatment of the gapped vector with Taq DNA polymerase avoids vector self-ligation," Yeast, 29(10):419-23 (2012).
Boch, "TALEs of genome targeting," Nature Biotechnology vol. 29, pp. 135-136 (2011).
Campbell et al., "Targeting protein function: the expanding toolkit for conditional disruption," Biochem J., 473(17):2573-2589 (2016).
Casini et al., "Bricks and blueprints: methods and standards for DNA assembly," Nat Rev Mol Cell Biol., (9):568-76 (2015).
Chica et al., "Semi-rational approaches to engineering enzyme activity: combining the benefits of directed evolution and rational design," Current Opinion in Biotechnology, 16(4): 378-384 (2005).
Durai et al., "Zinc finger nucleases: custom-designed molecular scissors for genome engineering of plant and mammalian cells", Nucleic Acids Res., 33(18):5978-90 (2005).
Kadonaga et al., "Regulation of RNA polymerase II transcription by sequence-specific DNA binding factors", Cell, 116(2):247-57 (2004).
Lee et al., "Targeted chromosomal deletions in human cells using zinc finger nucleases", Genome Res., 20(1): 81-9 (2009).
Miller et al., "A Tale nuclease architecture for efficient genome editing", Nature Biotechnology, 29 (2): 143-8 (2011).
Mittelman et al., "Zinc-finger directed double-strand breaks within CAG repeat tracts promote repeat instability in human cells", PNAS USA, 106 (24): 9607-12 (2009).
Shivange, "Advances in generating functional diversity for directed protein evolution", Current Opinion in Chemical Biology, 13 (1): 19-25 (2009).
Udo, "An Alternative Method to Facilitate cDNA Cloning for Expression Studies in Mammalian Cells by Introducing Positive Blue White Selection in Vaccinia Topoisomerase I-Mediated Recombination," PLoS One, 10(9):e0139349 (2015).
Urnov et al., "Genome editing with engineered zinc finger nucleases", Nature Reviews Genetics, 11:636-646 (2010).

International Search Report and Written Opinion for International Application No. PCT/US2018/053608, dated Dec. 13, 2018, p. 1-9.
International Search Report and Written Opinion for International Application No. PCT/US2018/053670, dated Jan. 3, 2019, p. 1-13.
International Search Report and Written Opinion for International Application No. PCT/US2018/053671, dated Sep. 26, 2018, p. 1-12.
International Search Report and Written Opinion for International Application No. PCT/US2018/040519, dated Sep. 26, 2018, p. 1-8.
International Search Report and Written Opinion for International Application No. PCT/US2019/026836, dated Jul. 2, 2019, p. 1-10.
International Search Report and Written Opinion for International Application No. PCT/US2019/023342, dated Jun. 6, 2019, p. 1-34.
International Search Report and Written Opinion for International Application No. PCT/US2019/030085, dated Jul. 23, 2019, p. 1-14.
International Search Report and Written Opinion for International Application No. PCT/US20/24341, dated Jun. 19, 2020, p. 1-9.
NonFinal Office Action for U.S. Appl. No. 16/399,988, dated Jul. 31, 2019, p. 1-20.
First Office Action Interview Pilot Program Pre-Interview Communication for U.S. Appl. No. 16/024,831, dated Feb. 12, 2019, p. 1-37.
NonFinal Office Action for U.S. Appl. No. 16/024,816 dated Sep. 4, 2018, p. 1-10.
Final Office Action for U.S. Appl. No. 16/024,816 dated Nov. 26, 2018, p. 1-12.
First Office Action Interview Pilot Program Pre-Interview Communication Preinterview for U.S. Appl. No. 16/454,865 dated Aug. 16, 2019, p. 1-36.
Yoshioka, et al., "Development of a mono-promoter-driven CRISPR/Cas9 system in mammalian cells", Scientific Reports, Jul. 3, 2015, p. 1-8.
Remaut, et al., "Plasmid vectors for high-efficiency expression controlled by the PL promoter of coliphage lambda," Laboratory of Molecular Biology, Apr. 15, 1981, p. 81-93.
International Search Report and Written Opinion for International Application No. PCT/US2019/028821, dated Aug. 2, 2019, p. 1-14.
International Search Report and Written Opinion for International Application No. PCT/US2019/028883, dated Aug. 16, 2019, p. 1-12.
International Search Report and Written Opinion for International Application No. PCT/US2019/46526, dated Dec. 18, 2019, p. 1-17.
International Search Report and Written Opinion for International Application No. PCT/US2018/34779, dated Nov. 26, 2018, p. 1-39.
International Search Report and Written Opinion for International Application No. PCT/US19/57250, dated Feb. 25, 2020, p. 1-16.
International Search Report and Written Opinion for International Application No. PCT/US19/47135, dated Jun. 11, 2020, p. 1-15.

* cited by examiner

EXAMPLE CREATE CASSETTES WITH LANDING PADS

Cre/Lox compatible CREATE cassette

Meganuclease/HDR compatible CREATE cassette

CRISPR EDITING TO EMBED NUCLEIC ACID LANDING PADS INTO GENOMES OF LIVE CELLS

RELATED CASES

This application claims priority to U.S. Ser. No. 63/078,789, filed 15 Sep. 2020, entitled "CRISPR EDITING TO EMBED NUCLEIC ACID LANDING PADS INTO GENOMES OF LIVE CELLS", which is incorporated herein in its entirety.

FIELD OF THE INVENTION

The present disclosure relates to compositions, methods, modules and automated integrated instrumentation for multiplex delivery of "landing pad" edits into the genome of a population of live cells.

INCORPORATION BY REFERENCE

Submitted with the present application is an electronically filed sequence listing via EFS-Web as an ASCII formatted sequence listing, entitled "INSC070US_seq_list_20210823", created Aug. 23, 2021, and 823 bytes in size. The sequence listing is part of the specification filed herewith and is incorporated by reference in its entirety.

BACKGROUND OF THE INVENTION

In the following discussion certain articles and methods will be described for background and introductory purposes. Nothing contained herein is to be construed as an "admission" of prior art. Applicant expressly reserves the right to demonstrate, where appropriate, that the articles and methods referenced herein do not constitute prior art under the applicable statutory provisions.

The ability to make precise, targeted changes to the genome of living cells has been a long-standing goal in biomedical research and development. Recently, various nucleases have been identified that allow for manipulation of gene sequences; hence gene function. The nucleases include nucleic acid-guided nucleases (i.e., CRISPR nucleases), which enable researchers to generate permanent edits in live cells; however, currently the payload that can be inserted is approximately 100 base pairs or less.

There is thus a need in the art of nucleic acid-guided nuclease editing for improved methods, compositions, modules and automated, integrated instruments to facilitate insertion of payloads greater than 100 base pairs into a cellular genome by leveraging a combination of high throughput nucleic acid-guided nuclease editing and lower-throughput recombinase/integrase or HDR-mediated insertion. The present disclosure addresses this need.

SUMMARY OF THE INVENTION

This Summary is provided to introduce a selection of concepts in a simplified form that are further described below in the Detailed Description. This Summary is not intended to identify key or essential features of the claimed subject matter, nor is it intended to be used to limit the scope of the claimed subject matter. Other features, details, utilities, and advantages of the claimed subject matter will be apparent from the following written Detailed Description including those aspects illustrated in the accompanying drawings and defined in the appended claims.

The present disclosure relates to methods, compositions, modules and automated multi-module cell processing instruments that allow one to perform nucleic acid-guided nuclease editing to embed "landing pads" into one or more—typically several to many—target loci in a population of cells in a multiplexed manner. The landing pads then can be leveraged to insert large DNA payloads (e.g., >100 bp) into the target loci. An advantage of the present methods and compositions is that they allow one to leverage CRISPR-type nucleic acid-guided nuclease genome-wide targeted editing to insert landing pads in the cellular genome, followed by insertion of large DNA sequences (e.g., >100 bp) via lower-throughput recombinase/integrase or HDR-mediated insertions or substitutions. The landing pads encode an enzyme recognition sequence such as a recombinase, integrase or meganuclease recognition sequence.

Thus, there is provided a method for multiplex insertion of large DNA payloads into a population of cells and identifying cells with a desired phenotype or genotype comprising the steps of: designing and synthesizing a library of editing cassettes comprising landing pads, wherein the editing cassettes further comprise a gRNA comprising homology to a target sequence in the cells and a repair template comprising 5' and 3' homology arms flanking the landing pad; inserting the library of editing cassettes into a vector backbone resulting in a library of editing vectors; transforming the population of cells with the library of editing vectors; allowing editing to take place in the population of cells to produce edited cells; transforming the edited cells with vectors carrying large DNA payloads, wherein the vectors carrying large DNA payloads further comprise a coding sequence for a recombinase or a meganuclease under control of an inducible promoter; inducing expression of the recombinase or a meganuclease to insert the large DNA payloads into the landing pads; and screening for cells comprising the desired phenotype or genotype.

In some embodiments of this method, the vectors carrying large DNA payloads comprise a coding sequence for a recombinase, the landing pads comprise a recognition sequence for the recombinase and the large DNA payloads comprise recognition sequences for the recombinase flanking the large DNA payload. In aspects of this embodiment, the recombinase is a cyclization recombination enzyme (Cre) and the landing pad and large DNA payload comprise lox recombination sites. Alternatively, the recombinase is flippase and the landing pad and large DNA payload comprise flippase recognition targets (FRTs).

In yet another embodiment of this method, the vectors carrying large DNA payloads comprise a coding sequence for a meganuclease, the landing pads comprise a recognition sequence for the meganuclease, and the large DNA payloads further comprise homologous recombination sequences flanking the DNA payloads. In some aspects, the meganuclease belongs to the LAGLIDADG family of nucleases, and in some aspects, the meganuclease is I-SceI; the meganuclease is I-CreI; or the meganuclease is I-DmoI.

In some embodiments of the method, the editing cassettes further comprise a barcode and/or an amplification priming site at the 3' end of the editing cassette. In some embodiments, the vectors carrying the large DNA payloads further comprise a selectable marker and the method further comprises a selection step between the transforming and allowing steps. In some aspects, the selectable marker in the vectors carrying the large DNA payloads is different from a selectable marker in the editing vectors.

In some aspects of the method, the vectors carrying the large DNA payloads comprise the coding sequence of the recombinase or meganuclease under the control of an inducible promoter. In some aspects, the inducible promoter is a pL promoter or a pBAD promoter.

In some aspects of the method, the vectors carrying large DNA payloads further comprise an origin of replication and a selectable marker.

In some embodiments, the large DNA payloads are from 100 bp to 100 Kb in length, and in some embodiments, the large DNA payloads are from 250 bp to 10 Kb in length.

In some embodiments, the screening step comprises polymerase chain reaction (PCR) analysis with appropriate primer sets; a metabolic test; measurement of transcript level; a phenotypic assay; detection of a protein product using an antibody specific to the protein product; or DNA sequencing of the integrated large DNA payload.

These aspects and other features and advantages of the invention are described below in more detail.

BRIEF DESCRIPTION OF THE DRAWINGS

The foregoing and other features and advantages of the present invention will be more fully understood from the following detailed description of illustrative embodiments taken in conjunction with the accompanying drawings in which.

It should be understood that the drawings are not necessarily to scale, and that like reference numbers refer to like features.

DETAILED DESCRIPTION

Figure 1A:
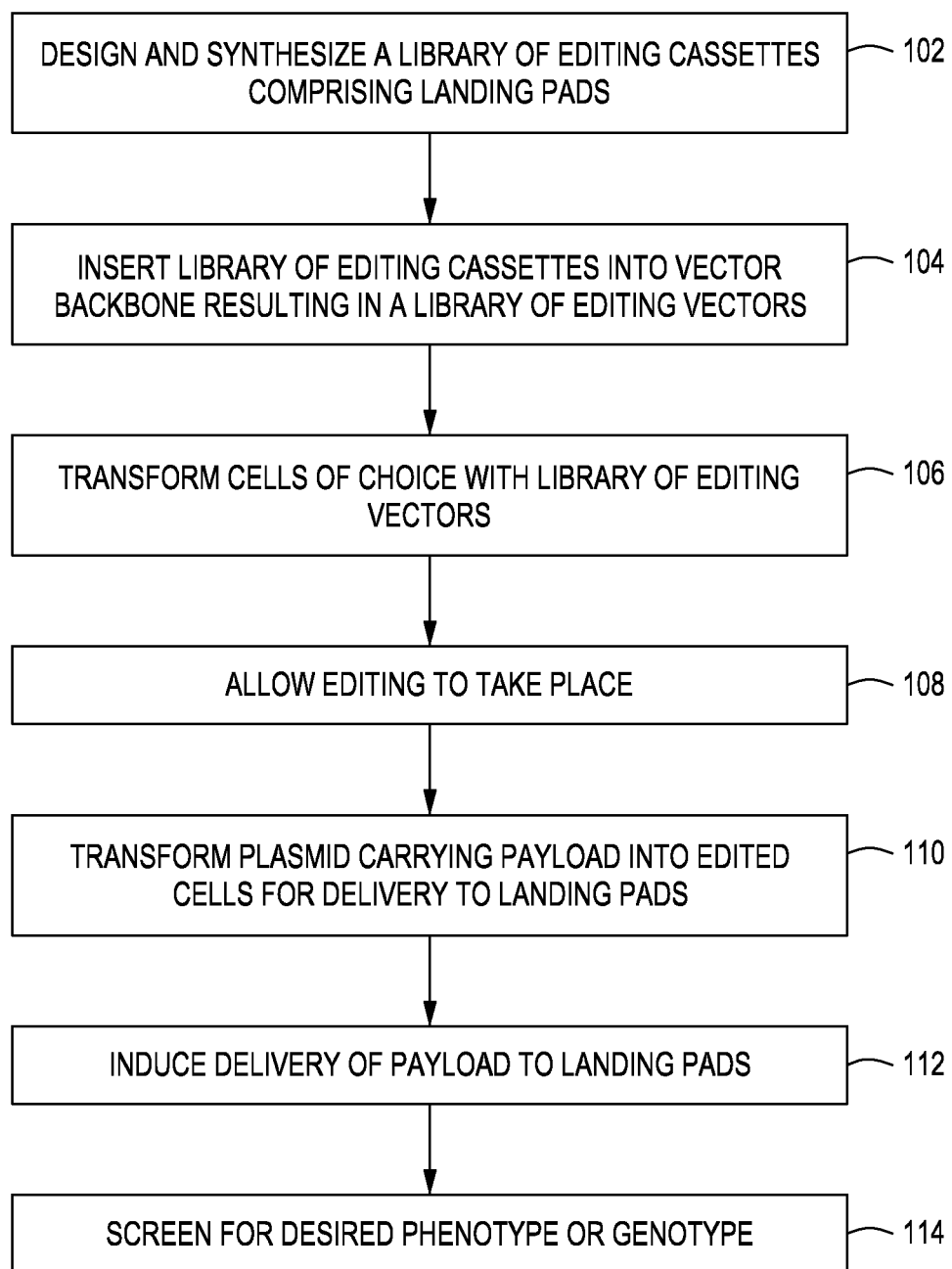
FIG. 1A is a simple process diagram for performing nucleic acid-guided nuclease editing in a population of cells to embed landing pads into target genetic loci in a population of cells, then leverage the landing pads to insert large DNA payloads (e.g., >100 bp) into the target loci.

All of the functionalities described in connection with one embodiment of the methods, devices or instruments described herein are intended to be applicable to the additional embodiments of the methods, devices and instruments described herein except where expressly stated or where the feature or function is incompatible with the additional embodiments. For example, where a given feature or function is expressly described in connection with one embodiment but not expressly mentioned in connection with an alternative embodiment, it should be understood that the feature or function may be deployed, utilized, or implemented in connection with the alternative embodiment unless the feature or function is incompatible with the alternative embodiment.

The practice of the techniques described herein may employ, unless otherwise indicated, conventional techniques and descriptions of molecular biology (including recombinant techniques), cell biology, biochemistry, and genetic engineering technology, which are within the skill of those who practice in the art. Such conventional techniques and descriptions can be found in standard laboratory manuals such as Green and Sambrook, *Molecular Cloning: A Laboratory Manual.* 4th ed., Cold Spring Harbor Laboratory Press, Cold Spring Harbor, N.Y., (2014); *Current Protocols in Molecular Biology*, Ausubel, et al. eds., (2017); Neumann, et al., *Electroporation and Electrofusion in Cell Biology*, Plenum Press, New York (1989); Chang, et al., *Guide to Electroporation and Electrofusion*, Academic Press, California (1992); *Viral Vectors* (Kaplift & Loewy, eds., Academic Press (1995)); all of which are herein incorporated in their entirety by reference for all purposes. For mammalian/stem cell culture and methods see, e.g., *Basic Cell Culture Protocols,* 4th ed. (Helgason & Miller, eds., Humana Press 2005); *Culture of Animal Cells*, Seventh Ed. (Freshney, ed., Humana Press 2016); *Microfluidic Cell Culture*, Second Ed. (Borenstein, Vandon, Tao & Charest, eds., Elsevier Press 2018); *Human Cell Culture* (Hughes, ed., Humana Press 2011); *3D Cell Culture* (Koledova, ed., Humana Press 2017); *Cell and Tissue Culture: Laboratory Procedures in Biotechnology* (Doyle & Griffiths, eds., John Wiley & Sons 1998); *Essential Stem Cell Methods*, (Lanza & Klimanskaya, eds., Academic Press 2011); *Essentials of Stem Cell Biology,* 3d ed., (Lanza & Atala, eds., Academic Press 2013); and *Handbook of Stem Cells*, (Atala & Lanza, eds., Academic Press 2012), all of which are herein incorporated in their entirety by reference for all purposes. CRISPR editing techniques can be found in, e.g., *Genome Editing and Engineering from TALENs and CRISPRs to Molecular Surgery*, Appasani and Church (2018); and *CRISPR: Methods and Protocols*, Lindgren and Charpentier (2015); both of which are herein incorporated in their entirety by reference for all purposes.

Note that as used herein and in the appended claims, the singular forms "a," "an," and "the" include plural referents unless the context clearly dictates otherwise. Thus, for example, reference to "a cell" refers to one or more cells, and reference to "the system" includes reference to equivalent steps, methods and devices known to those skilled in the art, and so forth. Additionally, it is to be understood that terms such as "left," "right," "top," "bottom," "front," "rear," "side," "height," "length," "width," "upper," "lower," "interior," "exterior," "inner," "outer" that may be used herein merely describe points of reference and do not necessarily limit embodiments of the present disclosure to any particular orientation or configuration. Furthermore, terms such as "first," "second," "third," etc., merely identify one of a number of portions, components, steps, operations, functions, and/or points of reference as disclosed herein, and likewise do not necessarily limit embodiments of the present disclosure to any particular configuration or orientation.

Unless defined otherwise, all technical and scientific terms used herein have the same meaning as commonly understood by one of ordinary skill in the art to which this invention belongs. All publications mentioned herein are incorporated by reference for the purpose of describing and disclosing devices, formulations and methodologies that may be used in connection with the presently described invention.

Where a range of values is provided, it is understood that each intervening value, between the upper and lower limit of that range and any other stated or intervening value in that stated range is encompassed within the invention. The upper and lower limits of these smaller ranges may independently be included in smaller ranges, and are also encompassed within the invention, subject to any specifically excluded limit in the stated range. Where the stated range includes one or both of the limits, ranges excluding either or both of those included limits are also included in the invention.

In the following description, numerous specific details are set forth to provide a more thorough understanding of the present invention. However, it will be apparent to one of skill in the art that the present invention may be practiced without one or more of these specific details. In other instances, features and procedures well known to those skilled in the art have not been described in order to avoid obscuring the invention. The terms used herein are intended to have the plain and ordinary meaning as understood by those of ordinary skill in the art.

The term "complementary" as used herein refers to Watson-Crick base pairing between nucleotides and specifically refers to nucleotides hydrogen bonded to one another with thymine or uracil residues linked to adenine residues by two hydrogen bonds and cytosine and guanine residues linked by three hydrogen bonds. In general, a nucleic acid includes a nucleotide sequence described as having a "percent complementarity" or "percent homology" to a specified second nucleotide sequence. For example, a nucleotide sequence may have 80%, 90%, or 100% complementarity to a specified second nucleotide sequence, indicating that 8 of 10, 9 of 10 or 10 of 10 nucleotides of a sequence are complementary to the specified second nucleotide sequence. For instance, the nucleotide sequence 3'-TCGA-5' is 100% complementary to the nucleotide sequence 5'-AGCT-3'; and the nucleotide sequence 3'-TCGA-5' is 100% complementary to a region of the nucleotide sequence 5'-TAGCTG-3'.

The term DNA "control sequences" refers collectively to promoter sequences, polyadenylation signals, transcription termination sequences, upstream regulatory domains, origins of replication, internal ribosome entry sites, nuclear localization sequences, enhancers, and the like, which collectively provide for the replication, transcription and translation of a coding sequence in a recipient cell. Not all of these types of control sequences need to be present so long as a selected coding sequence is capable of being replicated, transcribed and—for some components—translated in an appropriate host cell.

The terms "editing cassette", "CREATE cassette", "CREATE editing cassette", "CREATE fusion editing cassette" or "CFE editing cassette" refers to a nucleic acid molecule comprising a coding sequence for transcription of a guide nucleic acid or gRNA covalently linked to a coding sequence for transcription of a repair template.

The terms "guide nucleic acid" or "guide RNA" or "gRNA" refer to a polynucleotide comprising 1) a guide sequence capable of hybridizing to a genomic target locus, and 2) a scaffold sequence capable of interacting or complexing with a nucleic acid-guided nuclease.

"Homology" or "identity" or "similarity" refers to sequence similarity between two peptides or, more often in the context of the present disclosure, between two nucleic acid molecules. The term "homologous region" or "homology arm" refers to a region on the repair template with a certain degree of homology with the target genomic DNA sequence. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences.

A "landing pad" is a sequence of nucleotides inserted into a genome or episome of a cell via CRISPR editing comprising a recognition sequence.

The term "meganuclease" refers to an endodeoxyribonuclease characterized by a large recognition site (double-stranded DNA sequences of 12 to 40 base pairs) and as a result the recognition site generally occurs only once, if at all, in any given genome.

"Nucleic acid-guided editing components" refers to one, some, or all of a nucleic acid-guided nuclease or nickase fusion enzyme, a guide nucleic acid and a repair template.

"Operably linked" refers to an arrangement of elements where the components so described are configured so as to perform their usual function. Thus, control sequences operably linked to a coding sequence are capable of effecting the transcription, and in some cases, the translation, of a coding sequence. The control sequences need not be contiguous with the coding sequence so long as they function to direct the expression of the coding sequence. Thus, for example, intervening untranslated yet transcribed sequences can be present between a promoter sequence and the coding sequence and the promoter sequence can still be considered "operably linked" to the coding sequence. In fact, such sequences need not reside on the same contiguous DNA molecule (i.e. chromosome) and may still have interactions resulting in altered regulation.

A "PAM mutation" refers to one or more edits to a target sequence that removes, mutates, or otherwise renders inactive a PAM or spacer region in the target sequence.

A "promoter" or "promoter sequence" is a DNA regulatory region capable of binding RNA polymerase and initiating transcription of a polynucleotide or polypeptide coding sequence such as messenger RNA, ribosomal RNA, small nuclear or nucleolar RNA, guide RNA, or any kind of RNA. Promoters may be constitutive or inducible.

As used herein, the terms "protein" and "polypeptide" are used interchangeably. Proteins may or may not be made up entirely of amino acids.

"Recognition sequences" are particular sequences of nucleotides that a protein, DNA, or RNA molecule, or combinations thereof (such as, but not limited to, a restriction endonuclease, a modification methylase or a recombinase) recognizes and binds. For example, a recognition sequence for Cre recombinase is a 34 base pair sequence containing two 13 base pair inverted repeats (serving as the recombinase binding sites) flanking an 8 base pair core and designated loxP (see, e.g., Sauer, Current Opinion in Biotechnology, 5:521-527 (1994)). Other examples of recognition sequences include, but are not limited to, attB and attP, attR and attL and others that are recognized by the recombinase enzyme bacteriophage Lambda Integrase. The recombination site designated attB is an approximately 33 base pair sequence containing two 9 base pair core-type Int binding sites and a 7 base pair overlap region; attP is an approximately 240 base pair sequence containing core-type Int binding sites and arm-type Int binding sites as well as sites for auxiliary proteins IHF, FIS, and Xis (see, e.g., Landy, Current Opinion in Biotechnology, 3:699-7071 (1993)).

A "recombinase" is an enzyme that catalyzes the exchange of DNA segments at specific recombination sites. An "integrase" refers to a recombinase that is usually derived from viruses or transposons, as well as perhaps ancient viruses. "Recombination proteins" include excisive proteins, integrative proteins, enzymes, co-factors and associated proteins that are involved in recombination reactions using one or more recombination sites (again see, e.g., Landy, Current Opinion in Biotechnology, 3:699-707 (1993)). The recombination proteins used in the methods herein can be delivered to a cell via an expression cassette on an appropriate vector, such as a plasmid or viral vector. In other embodiments, recombination proteins can be delivered to a cell in protein form in the same reaction mixture used to deliver the desired nucleic acid(s). In yet other embodiments, the recombinase could also be encoded in the cell and expressed upon demand using a tightly controlled inducible promoter.

As used herein the terms "repair template" or "donor nucleic acid" or "donor DNA" or "homology arm" refer to 1) nucleic acid that is designed to introduce a DNA sequence modification (insertion, deletion, substitution) into a locus by homologous recombination using nucleic acid-guided nucleases, or 2) a nucleic acid that serves as a template (including a desired edit) to be incorporated into target DNA by reverse transcriptase in a CREATE fusion editing (CFE) system. For homology-directed repair, the repair template must have sufficient homology to the regions flanking the "cut site" or the site to be edited in the genomic target sequence. For template-directed repair, the repair template has homology to the genomic target sequence except at the position of the desired edit although synonymous edits may be present in the homologous (e.g., non-edit) regions. The length of the repair template(s) will depend on, e.g., the type and size of the modification being made. In many instances and preferably, the repair template will have two regions of sequence homology (e.g., two homology arms) complementary to the genomic target locus flanking the locus of the desired edit in the genomic target locus. Typically, an "edit region" or "edit locus" or "DNA sequence modification" region—the nucleic acid modification that one desires to be introduced into a genome target locus in a cell (e.g., the desired edit)—will be located between two regions of homology. The DNA sequence modification may change one or more bases of the target genomic DNA sequence at one specific site or multiple specific sites. A change may include changing 1, 2, 3, 4, 5, 10, 15, 20, 25, 30, 35, 40, 50, 75, 100, 150, 200, 300, 400, or 500 or more base pairs of the target sequence. A deletion or insertion may be a deletion or insertion of 1, 2, 3, 4, 5, 10, 15, 20, 25, 30, 40, 50, 75, 100, 150, 200, 300, 400, or 500 or more base pairs of the target sequence.

As used herein the term "selectable marker" refers to a gene introduced into a cell, which confers a trait suitable for artificial selection. General use selectable markers are well-known to those of ordinary skill in the art. Drug selectable markers such as ampicillin/carbenicillin, kanamycin, chloramphenicol, nourseothricin N-acetyl transferase, erythromycin, tetracycline, gentamicin, bleomycin, streptomycin, puromycin, hygromycin, blasticidin, and G418 may be employed. In other embodiments, selectable markers include, but are not limited to human nerve growth factor receptor (detected with a MAb, such as described in U.S. Pat. No. 6,365,373); truncated human growth factor receptor (detected with MAb); mutant human dihydrofolate reductase (DHFR; fluorescent MTX substrate available); secreted alkaline phosphatase (SEAP; fluorescent substrate available); human thymidylate synthase (TS; confers resistance to anti-cancer agent fluorodeoxyuridine); human glutathione S-transferase alpha (GSTA1; conjugates glutathione to the stem cell selective alkylator busulfan; chemoprotective selectable marker in CD34+ cells); CD24 cell surface antigen in hematopoietic stem cells; human CAD gene to confer resistance to N-phosphonacetyl-L-aspartate (PALA); human multi-drug resistance-1 (MDR-1; P-glycoprotein surface protein selectable by increased drug resistance or enriched by FACS); human CD25 (IL-2α; detectable by Mab-FITC); Methylguanine-DNA methyltransferase (MGMT; selectable by carmustine); rhamnose; and Cytidine deaminase (CD; selectable by Ara-C). "Selective medium" as used herein refers to cell growth medium to which has been added a chemical compound or biological moiety that selects for or against selectable markers.

The terms "target genomic DNA sequence", "target sequence", or "genomic target locus" and the like refer to any locus in vitro or in vivo, or in a nucleic acid (e.g., genome or episome) of a cell or population of cells, in which a change of at least one nucleotide is desired using a nucleic acid-guided nuclease editing system. The target sequence can be a genomic locus or extrachromosomal locus.

The terms "transformation", "transfection" and "transduction" are used interchangeably herein to refer to the process of introducing exogenous DNA into cells.

The term "variant" may refer to a polypeptide or polynucleotide that differs from a reference polypeptide or polynucleotide but retains essential properties. A typical variant of a polypeptide differs in amino acid sequence from another reference polypeptide. Generally, differences are limited so that the sequences of the reference polypeptide and the variant are closely similar overall and, in many regions, identical. A variant and reference polypeptide may differ in amino acid sequence by one or more modifications (e.g., substitutions, additions, and/or deletions). A variant of a polypeptide may be a conservatively modified variant. A substituted or inserted amino acid residue may or may not be one encoded by the genetic code (e.g., a non-natural amino acid). A variant of a polypeptide may be naturally occurring, such as an allelic variant, or it may be a variant that is not known to occur naturally.

A "vector" is any of a variety of nucleic acids that comprise a desired sequence or sequences to be delivered to and/or expressed in a cell. Vectors are typically composed of DNA, although RNA vectors are also available. Vectors include, but are not limited to, plasmids, fosmids, phagemids, virus genomes, BACs, YACs, PACs, synthetic chromosomes, and the like. In some embodiments, a coding sequence for a nucleic acid-guided nuclease is provided in a vector, referred to as an "engine vector." In some embodiments, the editing cassette may be provided in a vector, referred to as an "editing vector." In some embodiments, the coding sequence for the nucleic acid-guided nuclease and the editing cassette are provided in the same vector.

Nuclease-Directed Genome Editing Generally

The compositions, methods, modules and instruments described herein are employed to allow one to perform nucleic acid nuclease-directed genome editing (i.e., CRISPR editing) to introduce desired edits to a population of live cells. Specifically, the compositions, methods, modules and integrated instruments presented herein facilitate editing nucleotide sequences in a population of cells in a multiplexed and targeted manner, including insertions of large DNA sequences (e.g., >65 bp, >75 bp, or up to 100 bp—i.e., the insertion of "landing pads"), such that even larger insertions of nucleic acids can be made using a recombinase, an integrase or a meganuclease. An advantage of the present methods and compositions is that they allow one to leverage CRISPR-type nucleic acid-guided nuclease genome-wide targeted editing to insert landing pads in a cellular genome, followed by insertion of large DNA sequences (e.g., >100 bp) via lower-throughput recombinase/integrase or HDR-mediated insertions or substitutions into the inserted landing pads. The landing pads encode an enzyme recognition sequence such as a recombinase, integrase or meganuclease recognition sequence.

In CRISPR editing generally, a nucleic acid-guided nuclease complexed with an appropriate synthetic guide nucleic acid in a cell can cut the genome of the cell at a desired location. The guide nucleic acid helps the nucleic acid-guided nuclease recognize and cut the DNA at a specific target sequence. By manipulating the nucleotide sequence of the guide nucleic acid, the nucleic acid-guided nuclease may be programmed to target any DNA sequence for cleavage as long as an appropriate protospacer adjacent motif (PAM) is nearby. In certain aspects, the nucleic acid-guided nuclease editing system may use two separate guide nucleic acid molecules that combine to function as a guide nucleic acid, e.g., a CRISPR RNA (crRNA) and trans-activating CRISPR RNA (tracrRNA). In other aspects and preferably, the guide nucleic acid is a single guide nucleic acid construct that includes both 1) a guide sequence capable of hybridizing to a genomic target locus, and 2) a scaffold sequence capable of interacting or complexing with a nucleic acid-guided nuclease.

In general, a guide nucleic acid (e.g., gRNA) complexes with a compatible nucleic acid-guided nuclease and can then hybridize with a target sequence, thereby directing the nuclease to the target sequence. A guide nucleic acid can be DNA or RNA; alternatively, a guide nucleic acid may comprise both DNA and RNA. In some embodiments, a guide nucleic acid may comprise modified or non-naturally occurring nucleotides. In cases where the guide nucleic acid comprises RNA, the gRNA may be encoded by a DNA sequence on a polynucleotide molecule such as a plasmid, linear construct, or the coding sequence may and preferably does reside within an editing cassette. Methods and compositions for designing and synthesizing editing cassettes and libraries of editing cassettes are described in U.S. Pat. Nos. 10,240,167; 10,266,849; 9,982,278; 10,351,877; 10,364,442; 10,435,715; 10,465,207; 10,669,559; 10,711,284; 10,731,180; and 11,078,498; all of which are incorporated by reference herein.

A guide nucleic acid comprises a guide sequence, where the guide sequence is a polynucleotide sequence having sufficient complementarity with a target sequence to hybridize with the target sequence and direct sequence-specific binding of a complexed nucleic acid-guided nuclease to the target sequence. The degree of complementarity between a guide sequence and the corresponding target sequence, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences. In some embodiments, a guide sequence is about or more than about 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, 20 nucleotides in length. Preferably the guide sequence is 10-30 or 15-20 nucleotides long, or 15, 16, 17, 18, 19, or 20 nucleotides in length.

In general, to generate an edit in the target sequence, the gRNA/nuclease complex binds to a target sequence as determined by the guide RNA, and the nuclease recognizes a protospacer adjacent motif (PAM) sequence adjacent to the target sequence. The target sequence can be any polynucleotide endogenous or exogenous to the cell, or in vitro. For example, the target sequence can be a polynucleotide residing in the nucleus of the cell. A target sequence can be a sequence encoding a gene product (e.g., a protein) or a non-coding sequence (e.g., a regulatory polynucleotide, an intron, a PAM, a control sequence, or "junk" DNA).

The guide nucleic acid may be and preferably is part of an editing cassette that encodes the repair template that targets a cellular target sequence. Alternatively, the guide nucleic acid may not be part of the editing cassette and instead may be encoded on the editing vector backbone. For example, a sequence coding for a guide nucleic acid can be assembled or inserted into a vector backbone first, followed by insertion of the repair template in, e.g., an editing cassette. In other cases, the repair template in, e.g., an editing cassette can be inserted or assembled into a vector backbone first, followed by insertion of the sequence coding for the guide nucleic acid. Preferably, the sequence encoding the guide nucleic acid and the repair template are located together in a rationally-designed editing cassette and are simultaneously inserted or assembled via gap repair into a linear plasmid or vector backbone to create an editing vector.

The target sequence is associated with a proto-spacer mutation (PAM), which is a short nucleotide sequence recognized by the gRNA/nuclease complex. The precise preferred PAM sequence and length requirements for different nucleic acid-guided nucleases vary; however, PAMs typically are 2-10 or so base-pair sequences adjacent or in proximity to the target sequence and, depending on the nuclease, can be 5' or 3' to the target sequence. Engineering of the PAM-interacting domain of a nucleic acid-guided nuclease may allow for alteration of PAM specificity, improve target site recognition fidelity, decrease target site recognition fidelity, or increase the versatility of a nucleic acid-guided nuclease.

In most embodiments, genome editing of a cellular target sequence both introduces a desired DNA change to a cellular target sequence (an "intended" edit), e.g., the genomic DNA of a cell, and removes, mutates, or renders inactive a proto-spacer mutation (PAM) region in the cellular target sequence (an "immunizing edit") thereby rendering the target site immune to further nuclease binding. Rendering the PAM at the cellular target sequence inactive precludes additional editing of the cell genome at that cellular target sequence, e.g., upon subsequent exposure to a nucleic acid-guided nuclease complexed with a synthetic guide nucleic acid in later rounds of editing. Thus, cells having the desired cellular target sequence edit and an altered PAM can be selected for by using a nucleic acid-guided nuclease complexed with a synthetic guide nucleic acid complementary to the cellular target sequence. Cells that did not undergo the first editing event will be cut rendering a double-stranded DNA break, and thus will not continue to be viable. The cells containing the desired cellular target sequence edit and PAM alteration will not be cut, as these edited cells no longer contain the necessary PAM site and will continue to grow and propagate.

As for the nuclease component of the nucleic acid-guided nuclease editing system, a polynucleotide sequence encoding the nucleic acid-guided nuclease can be codon optimized for expression in particular cell types, such as bacterial, yeast, and mammalian cells. The choice of the nucleic acid-guided nuclease to be employed depends on many factors, such as what type of edit is to be made in the target sequence and whether an appropriate PAM is located close to the desired target sequence. CRISPR nucleases of use in the methods described herein include but are not limited to Cas 9, Cas 12/CpfI, MAD2, or MAD7, MAD 2007 or other MADzymes and MADzyme systems (see U.S. Pat. Nos. 9,982,279; 10,337,028; 10,435,714; 10,011,849; 10,626, 416; 10,604,746; 10,665,114; 10,640,754; 10,876,102; 10,883,077; 10,704,033; 10,745,678; 10,724,021; 10,767, 169; and 10,870,761 for sequences and other details related to engineered and naturally-occurring MADzymes).

Another component of the nucleic acid-guided nuclease system is the repair template comprising homology to the cellular target sequence. For the present methods and compositions, the repair template typically is on the same vector and in the same editing cassette as the guide nucleic acid and is under the control of the same promoter as the editing gRNA (that is, a single promoter driving the transcription of both the editing gRNA and the repair template). The repair template is designed to serve as a template for homologous recombination with a cellular target sequence nicked or cleaved by the nucleic acid-guided nuclease as a part of the gRNA/nuclease complex. A repair template polynucleotide may be of any suitable length, such as about or more than about 20, 25, 50, or 75 nucleotides in length. In certain preferred aspects, the repair template can be provided as an oligonucleotide of between 20-100 nucleotides, more preferably between 30-75 nucleotides. The repair template comprises two regions that are complementary to a portion of the cellular target sequence (e.g., homology arms) flanking the mutation or difference between the repair template and the cellular target sequence. When optimally aligned, the repair template overlaps with (is complementary to) the cellular target sequence by, e.g., about 20, 25, 30, 35, 40, 50, 60, 70, 80, 90 or more nucleotides. In the present methods and compositions, the repair template comprises at least one alteration compared to the cellular target sequence, such as a landing pad insertion compared to the cellular target sequence.

As described in relation to the gRNA, the repair template is provided as part of a rationally-designed editing cassette, which is inserted into an editing plasmid backbone where the editing plasmid backbone may comprise a promoter to drive transcription of the editing gRNA and the repair template when the editing cassette is inserted into the editing plasmid backbone. Moreover, there may be more than one, e.g., two, three, four, or more editing gRNA/repair template rationally-designed editing cassettes inserted into an editing vector targeting different regions of the genome; alternatively, a single rationally-designed editing cassette may comprise two to several editing gRNA/repair template pairs targeting different regions of the genome, where each editing gRNA is under the control of separate different promoters, separate like promoters, or where all gRNAs/repair template pairs are under the control of a single promoter. In some embodiments the promoter driving transcription of the editing gRNA and the repair template (or driving more than one editing gRNA/repair template pair) is optionally an inducible promoter.

In addition to the repair template, an editing cassette may comprise one or more primer binding sites. The primer binding sites are used to amplify the editing cassette by using oligonucleotide primers as described infra and may be biotinylated or otherwise labeled. In the current embodiments, the editing cassettes are a library of editing cassettes for, e.g., inserting a single landing pad into different target locations in the population of cells. Other embodiments envision performing successive rounds of editing where different landing pads are inserted throughout the genome of a population of cells; that is, in round 1, landing pad 1 is inserted, in round 2, landing pad 2 is inserted, and so on. In addition, the library of editing cassettes is cloned into vector backbones where, e.g., each different repair template may be associated with a different barcode. Also, in preferred embodiments, an editing vector or plasmid encoding components of the nucleic acid-guided nuclease system further encodes a nucleic acid-guided nuclease comprising one or more nuclear localization sequences (NLSs), such as about or more than about 1, 2, 3, 4, 5, 6, 7, 8, 9, 10, or more NLSs, particularly as an element of the nuclease sequence. In some embodiments, the engineered nuclease comprises NLSs at or near the amino-terminus, NLSs at or near the carboxy-terminus, or a combination.

Inserting and Leveraging Genomic Landing Pads

The present disclosure relates to methods, compositions, modules and automated multi-module cell processing instruments that allow one to perform nucleic acid-guided nuclease editing to embed "landing pads" into target loci in a population of cells in a multiplexed manner. Typically, a single landing pad type (e.g., a recognition sequence for a single enzyme) will be inserted into different loci in different cells resulting in a population of cells each with a landing pad inserted into a target region where the target regions are different in different cells. The landing pads then can be leveraged to insert large DNA payloads (e.g., >100 bp) into the target loci. An advantage of the present methods and compositions is that it allows one to leverage CRISPR-type nucleic acid-guided nuclease genome-wide targeted editing to insert landing pads in the cellular genome, followed by insertion of large DNA payloads (e.g., >100 bp) via lower-throughput recombinase/integrase or HDR-mediated insertions or substitutions. The landing pads encode an enzyme recognition sequence such as a recombinase, integrase or meganuclease recognition sequence.

FIG. 1A is a simple process diagram for performing nucleic acid-guided nuclease editing in a population of cells to embed landing pads into target genetic loci in a population of cells, then leverage the landing pads to insert large DNA payloads (e.g., >100 bp) into the target loci. In a first step 102 of method 100, a library of editing cassettes comprising paired gRNAs and repair templates is designed and synthesized. The editing cassettes each comprise a gRNA comprising both a guide and a spacer designed to target a specific locus in the cellular genome; a 5' homology arm; a recombinase recognition site or meganuclease recognition site; and a 3' homology arm (the recognition sequence forms the landing pad and the 5' homology arm, recognition sequence and 3' homology arm collectively form the landing pad repair template); and other desired sequences such as a barcode, primer amplification sites and the like. The various components of exemplary editing cassettes are described in more detail infra in relation to FIGS. 1C and 1D.

Once designed and synthesized 102, the library of editing cassettes is amplified (e.g., using primer amplification sites in the editing cassettes), purified and inserted 104 into a vector backbone—which in some embodiments may already comprise a coding sequence for the nucleic acid-guided nuclease—to produce a library of editing vectors. Alternatively, the coding sequence for the nuclease may be located on another vector that may be transformed into the cells before, at the same time as or after the editing vectors are transformed into the cells. In yet other alternatives, the coding sequence for the nuclease may be integrated into the cellular genome or the nuclease may be delivered to the cell as a protein. The vectors chosen for the methods herein will vary depending on the type of cells being edited and analyzed, where the vectors include, e.g., plasmids, BACs, YACs, viral vectors and synthetic chromosomes.

The cells of interest useful in the methods herein are any cells, including bacterial, yeast and animal (including mammalian) cells. Before being transformed by the editing vectors, the cells are often grown in culture for several passages. Cell culture is the process by which cells are grown under controlled conditions, almost always outside the cell's natural environment. For bacterial and yeast cells, the cells are typically grown in a defined medium in bulk culture. For mammalian cells, culture conditions typically vary somewhat for each cell type but generally include a medium and additives that supply essential nutrients such as amino acids, carbohydrates, vitamins, minerals, growth factors, hormones, and gases such as, e.g., $O_2$ and $CO_2$. In addition to providing nutrients, the medium typically regulates the physio-chemical environment via a pH buffer and most cells are grown at 37° C. Many mammalian cells require or prefer a surface or artificial substrate on which to grow (e.g., adherent cells), whereas other cells such as hematopoietic cells and some adherent cells can be grown in or adapted to grow in suspension. Adherent cells often are grown in 2D monolayer cultures in petri dishes or flasks, but some adherent cells can grow in suspension cultures to higher density than would be possible in 2D cultures. "Passages" generally refers to transferring a small number of cells to a fresh substrate with fresh medium, or, in the case of suspension cultures, transferring a small volume of the culture to a larger volume of medium.

The cells of choice are provided and are transformed with the library of editing vectors 106. The library of editing vectors comprises vector backbones each "carrying" at least one editing cassette. For single edits where one landing pad is inserted per cell, the edit (e.g., landing pad) is the same for every cassette in the library, but the landing pad is targeted to different locations around the genome. The library of editing cassettes may have tens, hundreds, thousands, tens of thousands or more different editing cassettes (in this case, tens, hundreds, thousands, tens of thousands or more different guides), where the landing pad sequences are the same but the gRNA and homology arms are different for insertion into different genomic target loci.

As used herein, transformation is intended to generically include a variety of art-recognized techniques for introducing an exogenous nucleic acid sequence (e.g., an engine and/or editing vector) into a target cell, and the term "transformation" as used herein includes all transformation and transfection techniques. Such methods include, but are not limited to, electroporation, lipofection, optoporation, injection, microprecipitation, microinjection liposomes, particle bombardment, sonoporation laser-induced poration bead transfection, calcium phosphate or calcium chloride coprecipitation, or DEAE-dextran-mediated transfection. Cells can also be prepared for vector uptake using, e.g., a sucrose, sorbitol or glycerol wash. Additionally, hybrid techniques that exploit the capabilities of mechanical and chemical transfection methods can be used. e.g., magnetofection, a transfection methodology that combines chemical transfection with mechanical methods. In another example, cationic lipids may be deployed in combination with gene guns or electroporators. Suitable materials and methods for transforming or transfecting target cells can be found, e.g., in Green and Sambrook, *Molecular Cloning: A Laboratory Manual*, 4th ed., Cold Spring Harbor Laboratory Press, Cold Spring Harbor, N.Y. (2014).

Once transformed 106, the cells are allowed to recover and selection optionally is performed to select for cells transformed with the editing vector, which most often comprises a selectable marker. At a next step 108, editing is allowed to take place. If one or both components of the editing machinery (e.g., editing cassette and nuclease) is under the control of an inducible promoter, conditions are provided to induce editing. If none of the components of the editing machinery are under the control of an inducible promoter, editing proceeds immediately after transformation. During the editing process, many cells may die due to double-strand breaks in the genome that are a consequence of the editing process. Of the cells that do survive editing and continue to grow, the surviving cells will comprise a landing pad that allows for insertions or substitutions of large payloads.

After editing takes place and after recovery and growth for 1-4 hours, or typically 8, 10 or 14 hours in rich medium and optional antibiotic selection at 15-37° C. (depending on cell type), the cells are grown and prepared for another round of transformation, this time with a plasmid or vector carrying 1) a coding sequence for the appropriate recombinase/integrase or meganuclease targeting the landing pad recognition sequence; and 2) either a large payload sequence flanked by either the recombinase or integrase recognition sequence for recombinase/integrase-mediated insertion into the landing pad in the genome, or a large payload sequence flanked by homology arm sequences for HDR-mediated insertion into the genome via the meganuclease 110. FIGS. 1E and 1F described infra depict the payload vectors in more detail. Typically the recombinase or meganuclease is under the control of an inducible promoter such that the expression of the recombinase or meganuclease is tightly controlled. At step 112, expression of the recombinase or meganuclease is induced, thereby inducing the delivery of the large payload to the landing pad.

Figure 1B:
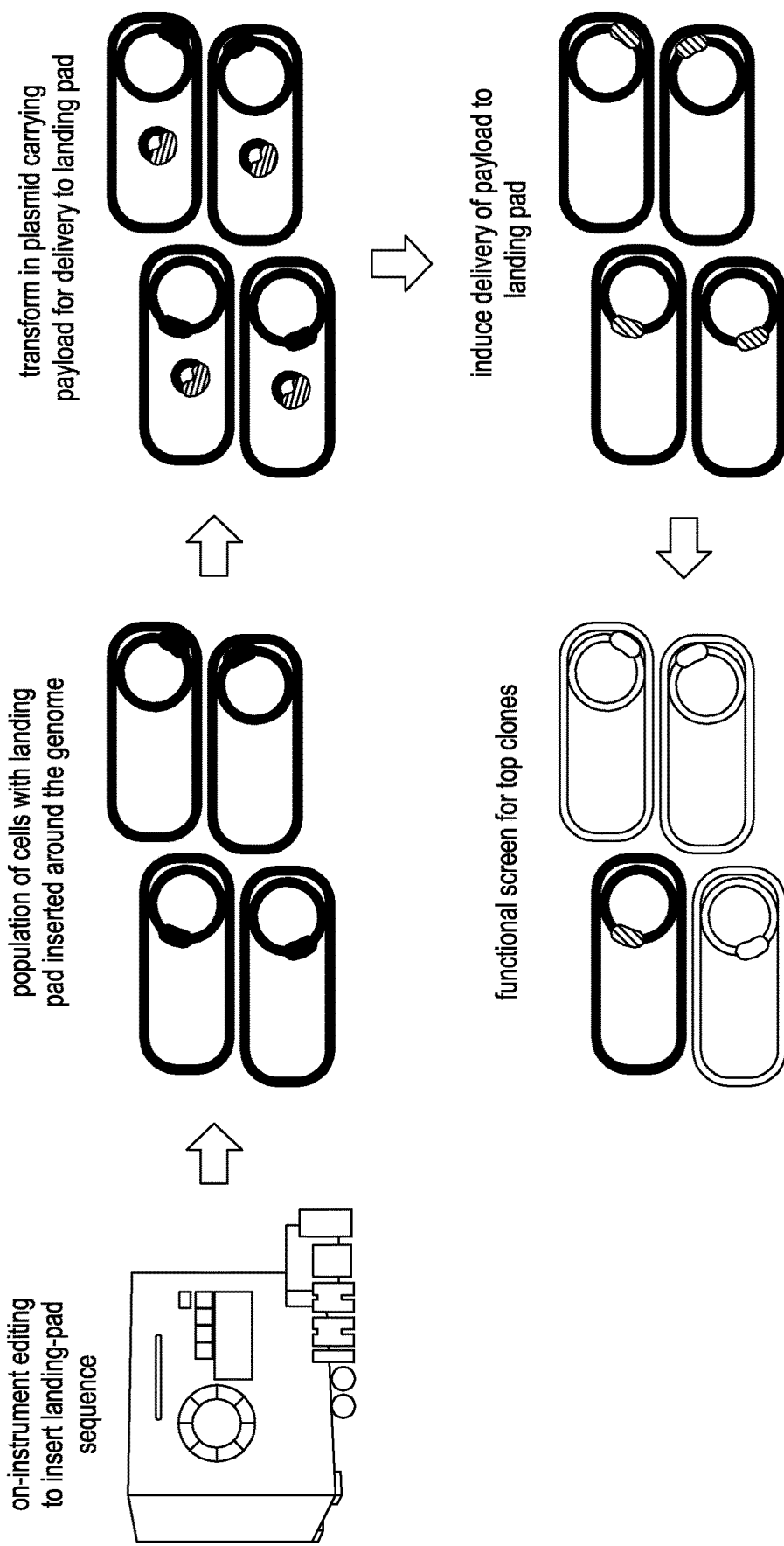
FIG. 1B is a simplified depiction of the process described in FIG. 1A.

FIG. 1B is a simplified diagram of the process described in FIG. 1A. The method begins with multiplexed CRISPR-based editing of a cell population using editing vectors comprising the CREATE editing cassettes, preferably in an automated manner using an instrument (depicted at left) such as described U.S. Pat. Nos. 10,253,316; 10,329,559; 10,323,242; 10,421,959; 10,465,185; 10,519,437; 10,584,333; 10,584,334; 10,647,982; 10,689,645; 10,738,301; 10,738,663; 10,947,532; 10,894,958; 10,954,512; and 11,034,953; and U.S. Ser. No. 17/239,540. Again, the library of editing cassettes may have tens, hundreds, thousands, tens of thousands or more different editing cassettes, where the landing pad sequences are the same but the gRNA and repair templates are different for insertion into different genomic target loci. After editing, the population of cells comprise a genome with landing pads inserted into different loci around the genome, depicted as a black bar on a circular genome in the cell.

Following insertion of the landing pads into various loci in the genome, the cells are then transformed with a plasmid or other vector carrying the payload to be delivered to the landing pads (depicted as striped bars on the vectors in the cells). As described above, transformation is intended to generically include a variety of art-recognized techniques for introducing an exogenous nucleic acid sequence (e.g., an engine and/or editing vector) into a target cell, and the term "transformation" as used herein includes all transformation and transfection techniques. Each plasmid or vector comprises 1) a coding sequence for the appropriate recombinase/integrase or meganuclease targeting the landing pad recognition sequence; and 2) either a large payload sequence flanked by either the recombinase or integrase recognition sequence for recombinase/integrase-mediated insertion into the landing pad in the genome, or a large payload sequence flanked by homology arm sequences for HDR-mediated insertion into the genome via the meganuclease. In an optional (but preferred) step, the plasmid or vector also comprises a coding sequence for a selection marker and the cells are selected after transformation.

After transformation and optional selection, delivery of the large payloads to the landing pads in the cells is induced by inducing expression of the recombinase/integrase or meganuclease. The cells with the payload delivered to the landing pads are allowed to recover and grow and then are screened. Note that after delivery of the payload to the landing pads, the black bar on the chromosome in the cells is transformed into a striped bar. Screening for proper integration of the payload includes but is not limited to 1) polymerase chain reaction (PCR) analysis with appropriate primer sets used to assess whether the delivery vector was correctly integrated at the target site; 2) assessment of activity of the nucleic acid of interest, including but not limited to a metabolic test, measurement of transcript level, a phenotypic assay, or detection of a protein product using an antibody specific to the protein product; and/or 3) DNA sequencing of the integrated payload. Exemplary applications of the present compositions and methods include genome-wide delivery of large-insert promoter libraries; delivery of heterologous genes or pathways to a large number of genomic locations enabling examination of location-dependent expression effects; and delivery of fusion-protein partners to multiple loci around the genome.

Figure 1C:
FIG. 1C is an exemplary editing cassette used to embed a landing pad into a target genome in a cell facilitating subsequent insertion of a large payload via a sequence-specific recombinase/integrase.

FIG. 1C is an exemplary editing cassette used to embed a landing pad into a target genome in a cell allowing insertion of a large payload via a sequence-specific recombinase/integrase. In the sequence-specific recombinase/integrase embodiment, the editing cassette (e.g., CREATE cassette) comprises from 5' to 3' 1) the gRNA (guide+spacer); and 2) a repair template comprising a 5' homology arm "wing"; a sequence recognized by a recombinase or integrase (in this case, a loxP sequence recognized by the Cre recombinase); a 3' homology arm "wing"; and a "P2" priming site. Optionally, the editing cassette may also comprise a barcode positioned between the 3' homology arm "wing" and the "P2" priming site. The sequence recognized by the recombinase or integrase is the landing pad and the combination of the 5' homology arm "wing", the sequence recognized by a recombinase or integrase, and the 3' homology arm "wing" is the "repair template" or "landing pad repair template" which is inserted or substituted into the target sequence in the cellular genome.

Site/sequence-specific recombination differs from general homologous recombination in that short specific DNA sequences, which are required for recognition by a recombinase, are the only sites at which recombination occurs. Depending on the orientations of these sites on a particular DNA strand or chromosome, the specialized recombinases that recognize these specific sequences can catalyze 1) DNA excision or 2) DNA inversion or rotation. Site-specific recombination can also occur between two DNA strands if these sites are not present on the same chromosome. A number of bacteriophage- and yeast-derived site-specific recombination systems—each comprising a recombinase and specific cognate sites—have been shown to work in both prokaryotic and eukaryotic cells including the bacteriophage P1 Cre/lox system, yeast FLP-FRT system, and the Dre system of the tyrosine family of site-specific recombinases. Such systems and methods of use are described, e.g., in U.S. Pat. Nos. 7,422,889; 7,112,715; 6,956,146; 6,774,279; 5,677,177; 5,885,836; 5,654,182; and 4,959,317, each of which is incorporated herein by reference to teach methods of using such recombinases. Other systems that may be utilized in the compositions and methods described herein include those of the tyrosine family of site-specific recombinases such as bacteriophage lambda integrase, HK2022 integrase; as well as systems belonging to the separate serine family of recombinases such as bacteriophage phiC31 and R4Tp901 integrases.

The methods of the invention preferably utilize combined variants of the sequence-specific recombination sites that are recognized by the same recombinase for recombinase-mediated cassette exchange (RMCE). RMCE is a convenient method for genetic manipulation; however, in order to achieve recombination in a desired direction, recognition site mutants are used. Examples of such sequence-specific recombination site variants include those that contain a combination of inverted repeats or those which comprise recombination sites having mutant spacer sequences. For example, two classes of variant recombinase sites are available to engineer stable Cre-loxP integrative recombination. Both exploit sequence mutations in the Cre recognition sequence, either within the 8 bp spacer region or the 13 bp inverted repeats. Spacer mutants such as lox511 (Hoess, et al., Nucleic Acids Res, 14:2287-2300 (1986)), lox5171 and lox2272 (Lee and Saito, Gene, 216:55-65 (1998)), m2, m3, m7, and m11 (Langer, et al., Nucleic Acids Res, 30:3067-3077 (2002)) recombine readily with themselves but have a markedly reduced rate of recombination with the wild-type site. This class of mutants has been exploited for DNA insertion by RMCE using non-interacting Cre-Lox recombination sites and non-interacting FLP recombination sites (Baer and Bode, Curr Opin Biotechnol, 12:473-480 (2001); Albert, et al., Plant J, 7:649-659 (1995); Seibler and Bode, Biochemistry, 36:1740-1747 (1997); Schlake and Bode, Biochemistry, 33:12746-12751 (1994)). For example, exemplary lox variant sequences are shown in Table 1:

TABLE 1

| Lox Variant | Spacer sequence |
|---|---|
| Lox2272 | AAGTATCC |
| Lox5171 | ATGTGTAC |
| LoxM2 | AGAAACCA |
| LoxP | ATGTATGC |

Figure 1D:
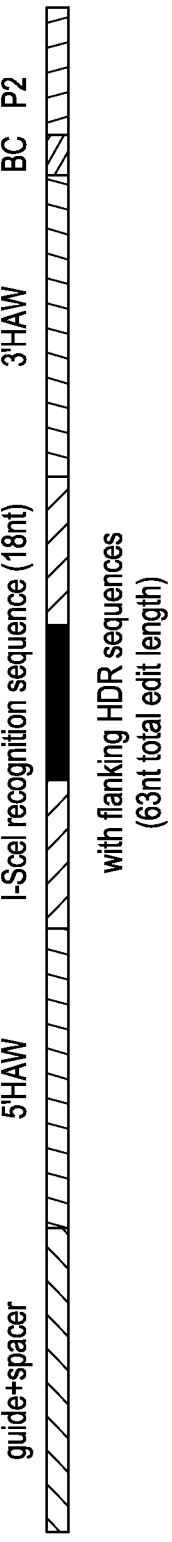
FIG. 1D is an exemplary editing cassette used to embed a landing pad into a target genome in a cell facilitating subsequent insertion of a large payload via a meganuclease system.
Figures 1E, 1F:
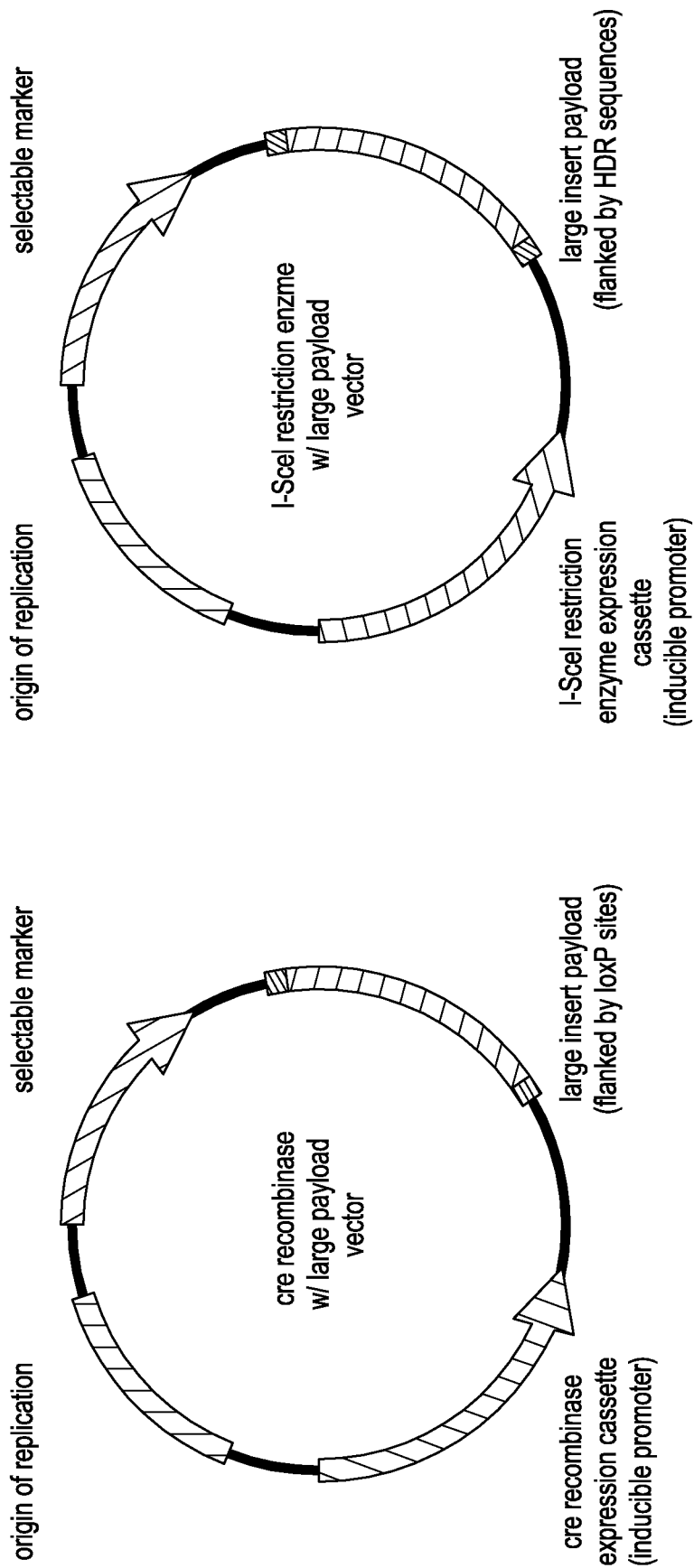
FIG. 1E is an exemplary vector for inserting a large DNA sequence into an embedded landing pad via a recombinase.
FIG. 1F is an exemplary vector for inserting a large DNA payload into an embedded landing pad via a meganuclease.

FIG. 1D is an exemplary editing cassette used to embed a landing pad into a target genome in a cell which allows insertion of a large payload via a meganuclease. In the meganuclease embodiment, the editing cassette (e.g., CREATE cassette) comprises from 5' to 3' 1) the gRNA (guide+spacer); and 2) a repair template comprising a 5' homology arm "wing"; a sequence recognized by a meganuclease (in this case, an I-SceI recognition sequence); a 3' homology arm "wing"; and a "P2" priming site. Optionally, the editing cassette may also comprise a barcode positioned between the 3' homology arm "wing" and the "P2" priming site. The sequence recognized by the meganuclease is the landing pad and the combination of the 5' homology arm "wing", the sequence recognized by a meganuclease, and the 3' homology arm "wing" is the "repair template" which is inserted or substituted into the target sequence in the cellular genome.

Meganucleases are endodeoxyribonucleases characterized by a large recognition site (double-stranded DNA sequences of 12 to 40 base pairs). As a result of the large recognition sequence, a meganuclease recognition site generally occurs only once if at all in any given genome. For example, the 18-base pair sequence recognized by the I-SceI meganuclease on average requires a genome twenty times the size of the human genome to be found once by chance (although sequences with a single mismatch occur about three times per human-sized genome). I-SceI recognizes an 18-base pair sequence TAGGGATAACAGGGTAAT and leaves a 4 base pair 3' hydroxyl overhang. Meganucleases are therefore considered to be the most specific naturally-occurring restriction enzymes. Among meganucleases, the LAGLIDADG family of homing endonucleases has become a valuable tool for the study of genomes and genome engineering over the past fifteen years. Meganucleases are "molecular DNA scissors" that can be used to replace, eliminate or modify sequences in a highly targeted way. By modifying the meganuclease recognition sequence through protein engineering, the targeted sequence can be changed. Meganucleases are used to modify all genome types, whether bacterial, plant or animal.

There are five families, or classes, of homing endonucleases; the most widespread and best known of which is the LAGLIDADG family. The name of this family corresponds to an amino acid sequence (or motif) that is found, more or less conserved, in all the proteins of this family. These small proteins are also known for their compact and closely packed three-dimensional structures. The best characterized endonucleases which are most widely used in research and genome engineering include I-SceI (discovered in *Saccharomyces cerevisiae*), I-CreI (from the chloroplasts of the green algae *Chlamydomonas reinhardtii*) and I-DmoI (from the archaebacterium *Desulfurococcus mobilis*). The high specificity of meganucleases gives them a high degree of precision and much lower cell toxicity than other naturally occurring restriction enzymes.

FIG. 1E is an exemplary vector for inserting a large DNA payload into an embedded landing pad via a recombinase (see FIG. 1C). The exemplary vector comprises, starting at 10 o'clock and continuing clockwise, an origin of replication for the plasmid such as a bacterial or yeast origin of replication for propagation of the plasmid in, e.g., *E. coli* or *S. cerevisiae*; a selectable marker that is preferably different than the selectable marker(s) used in the editing vector (and, e.g., engine vector, if used); the large insert payload flanked by recognition sequences (in this case, loxP sites); and a coding sequence for the recombinase (here, cre) under the control of an inducible promoter.

The large payload insert is limited in size by the delivery vector but may comprise more than 60 bp, more than 70 bp, more than 80 bp, more than 90 bp, more than 100 bp, more than 150 bp, more than 200 bp; up to 10 Kb, 15 Kb or 20 Kb for plasmids and up to 100 Kb for YAC and BAC vectors; and greater for artificial chromosomes.

Expression of the recombinase is controlled preferably by an inducible promoter to tightly control expression; examples of inducible promoters include the pL promoter, which is induced by an increase in temperature; the pBAD promoter, which is induced by the addition of arabinose to the growth medium; the tetracycline-controlled transcriptional activation system (Tet-On/Tet-Off, Clontech, Inc. (Palo Alto, Calif.); Bujard and Gossen, PNAS, 89(12):5547-5551 (1992)); the Lac Switch Inducible system (Wyborski et al., Environ Mol Mutagen, 28(4):447-58 (1996); DuCoeur et al., Strategies 5(3):70-72 (1992); and U.S. Pat. No. 4,833,080); the ecdysone-inducible gene expression system (No et al., PNAS, 93(8):3346-3351 (1996)); the cumate gene-switch system (Mullick et al., BMC Biotechnology, 6:43 (2006)); and the tamoxifen-inducible gene expression (Zhang et al., Nucleic Acids Research, 24:543-548 (1996)) as well as others.

As described above, an alternative to utilizing a recombinase/integrase is utilizing a meganuclease (see FIG. 1D). FIG. 1F is an exemplary vector for inserting a large DNA sequence into an embedded landing pad via a meganuclease. The exemplary vector comprises, starting at 10 o'clock and continuing clockwise, an origin of replication for the plasmid such as a bacterial or yeast origin of replication for propagation of the plasmid in, e.g., *E. coli* or *S. cerevisiae*; a selectable marker that is preferably different than the selectable markers used in the editing vector (and, e.g., engine vector, if used); the large insert payload flanked by HDR sequences compatible with the HDR sequences flanking the I-SceI recognition sequence of FIG. 1D; and a coding sequence for the recombinase (here, the I-SceI restriction enzyme) under the control of an inducible promoter. As with the vector depicted in FIG. 1E, the large payload insert is limited in size by the delivery vector but may comprise more than 60 bp, more than 70 bp, more than 80 bp, more than 90 bp, more than 100 bp, more than 150 bp, more than 200 bp, and up to 10 Kb, 15 Kb or 20 Kb for plasmids and up to 100 Kb for YAC and BAC vectors and expression of the recombinase is controlled preferably by an inducible promoter to tight control of expression.

The meganuclease cuts the landing pad and the large payload serves as the repair template by way of its flanking arms. Yeast has a natural repair capability; however *E. coli* can be engineered to comprise, e.g., the λ Red repair machinery to drive HDR repair.

Figure 2A:
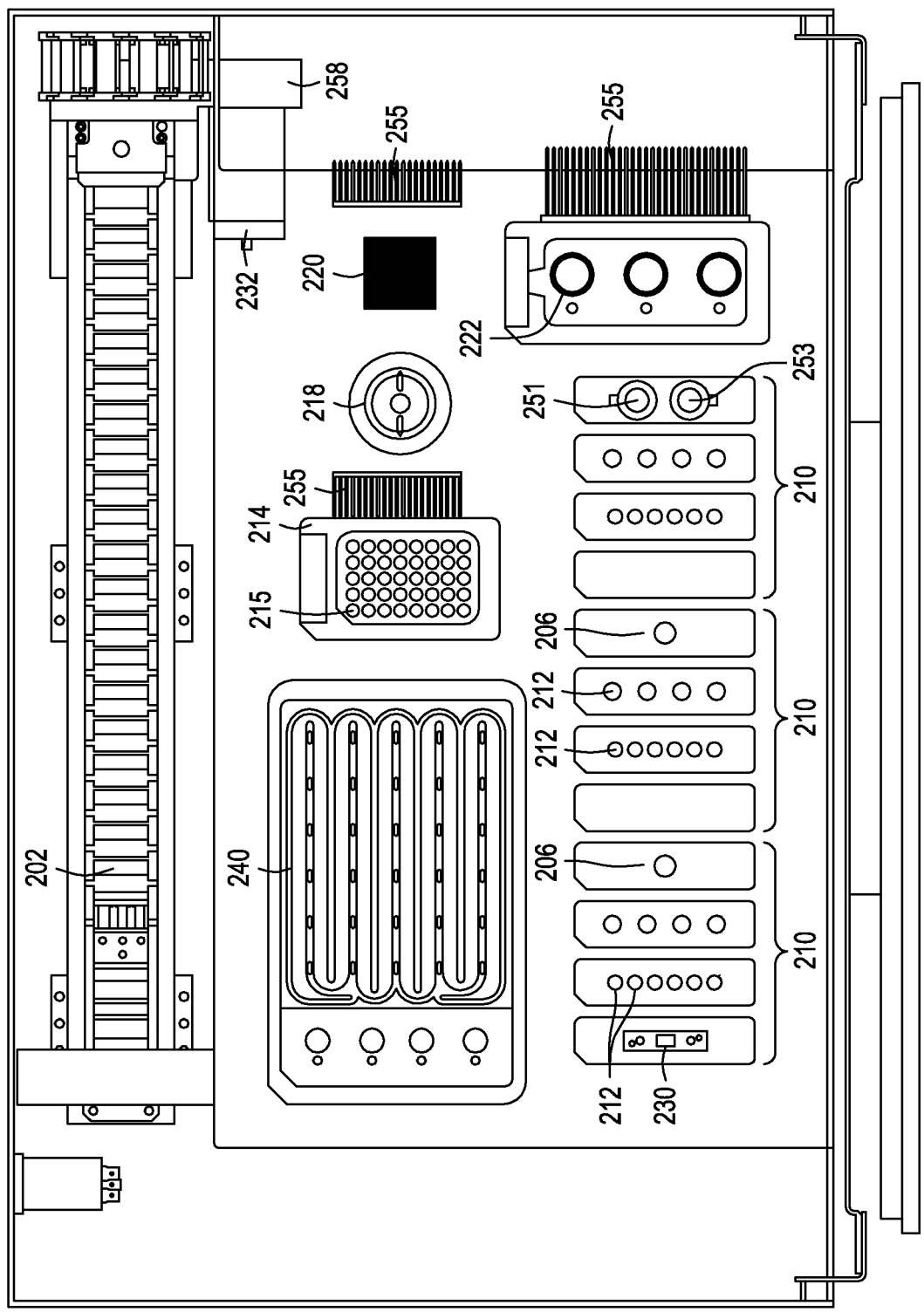
FIGS. 2A-2C depict three different views of an exemplary automated multi-module cell processing instrument for performing nucleic acid-guided nuclease editing.

Automated Cell Editing Instruments and Modules to Perform Nucleic Acid-Guided Nuclease or Nickase Fusion Editing in Cells One Embodiment of an Automated Cell Editing Instrument FIG. 2A depicts an exemplary automated multi-module cell processing instrument 200 to, e.g., perform targeted gene editing of live cells. The instrument 200, for example, may be and preferably is designed as a stand-alone benchtop instrument for use within a laboratory environment. The instrument 200 may incorporate a mixture of reusable and disposable components for performing the various integrated processes in conducting automated genome cleavage and/or editing in cells without human intervention. Illustrated is a gantry 202, providing an automated mechanical motion system (actuator) (not shown) that supplies XYZ axis motion control to, e.g., an automated (i.e., robotic) liquid handling system 258 including, e.g., an air displacement pipettor 232 which allows for cell processing among multiple modules without human intervention. In some automated multi-module cell processing instruments, the air displacement pipettor 232 is moved by gantry 202 and the various modules and reagent cartridges remain stationary; however, in other embodiments, the liquid handling system 258 may stay stationary while the various modules and reagent cartridges are moved. Also included in the automated multi-module cell processing instrument 200 are reagent cartridges 210 (see, U.S. Pat. Nos. 10,376,889; 10,406,525; 10,478,822; 10,576,474; 10,639,637; 10,738, 271; and 10,799,868) comprising reservoirs 212 and transformation module 230 (e.g., a flow-through electroporation device as described in U.S. Pat. Nos. 10,435,713; 10,443,074; and 10,851,389), as well as wash reservoirs 206, cell input reservoir 251 and cell output reservoir 253. The wash reservoirs 206 may be configured to accommodate large tubes, for example, wash solutions, or solutions that are used often throughout an iterative process. Although two of the reagent cartridges 210 comprise a wash reservoir 206 in FIG. 2A, the wash reservoirs instead could be included in a wash cartridge where the reagent and wash cartridges are separate cartridges. In such a case, the reagent cartridge and wash cartridge may be identical except for the consumables (reagents or other components contained within the various inserts) inserted therein.

In some implementations, the reagent cartridges 210 are disposable kits comprising reagents and cells for use in the automated multi-module cell processing/editing instrument 200. For example, a user may open and position each of the reagent cartridges 210 comprising various desired inserts and reagents within the chassis of the automated multi-module cell editing instrument 200 prior to activating cell processing. Further, each of the reagent cartridges 210 may be inserted into receptacles in the chassis having different temperature zones appropriate for the reagents contained therein.

Also illustrated in FIG. 2A is the robotic liquid handling system 258 including the gantry 202 and air displacement pipettor 232. In some examples, the robotic handling system 258 may include an automated liquid handling system such as those manufactured by Tecan Group Ltd. of Mannedorf, Switzerland, Hamilton Company of Reno, Nev. (see, e.g., WO2018015544A1), or Beckman Coulter, Inc. of Fort Collins, Colo. (see, e.g., US20160018427A1). Pipette tips 215 may be provided in a pipette transfer tip supply 214 for use with the air displacement pipettor 232. The robotic liquid handling system allows for the transfer of liquids between modules without human intervention.

Inserts or components of the reagent cartridges 210, in some implementations, are marked with machine-readable indicia (not shown), such as bar codes, for recognition by the robotic handling system 258. For example, the robotic liquid handling system 258 may scan one or more inserts within each of the reagent cartridges 210 to confirm contents. In other implementations, machine-readable indicia may be marked upon each reagent cartridge 210, and a processing system (not shown, but see element 237 of FIG. 2B) of the automated multi-module cell editing instrument 200 may identify a stored materials map based upon the machine-readable indicia. In the embodiment illustrated in FIG. 2A, a cell growth module comprises a cell growth vial 218 (for details, see U.S. Pat. Nos. 10,435,662; 10,433,031; 10,590,375; 10,717,959; and 10,883,095). Additionally seen is a tangential flow filtration (TFF) module 222 (for details, see U.S. Ser. Nos. 16/516,701 and 16/798,302). Also illustrated as part of the automated multi-module cell processing instrument 200 of FIG. 2A is a singulation module 240 (e.g., a solid wall isolation, incubation and normalization device (SWIIN device)) shown here and described in detail in U.S. Pat. Nos. 10,533,152; 10,633,626; 10,633,627; 10,647,958; 10,723,995; 10,801,008; 10,851,339; 10,954,485; 10,532,324; 10,625,212; 10,774,462; and 10,835,869), served by, e.g., robotic liquid handing system 258 and air displacement pipettor 232. Additionally seen is a selection module 220 which may employ magnet separation. Also note the placement of three heatsinks 255.

Figure 2B:
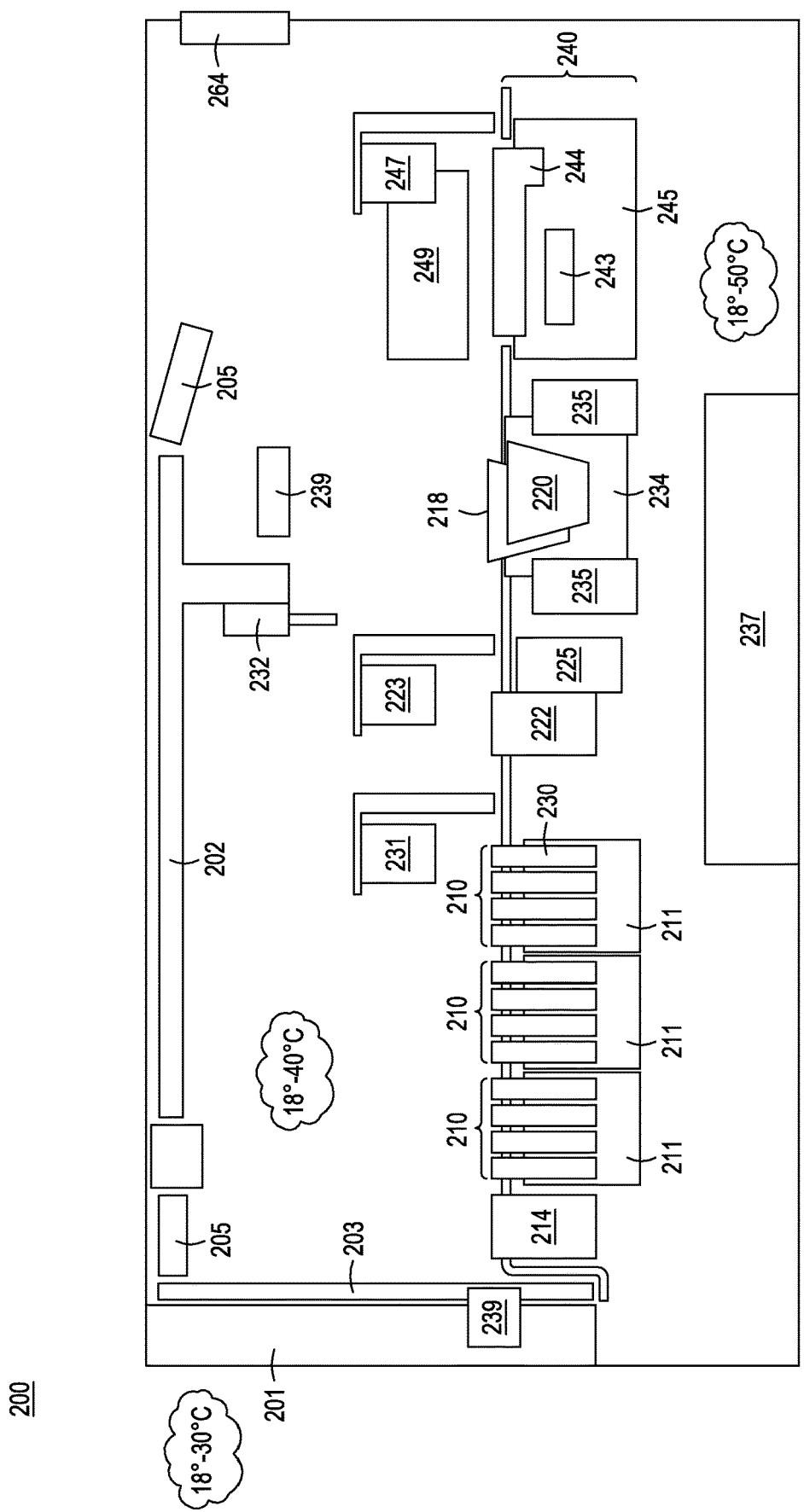

FIG. 2B is a simplified representation of the contents of the exemplary multi-module cell processing instrument 200 depicted in FIG. 2A. Cartridge-based source materials (such as in reagent cartridges 210), for example, may be positioned in designated areas on a deck of the instrument 200 for access by an air displacement pipettor 232. The deck of the multi-module cell processing instrument 200 may include a protection sink (not shown) such that contaminants spilling, dripping, or overflowing from any of the modules of the instrument 200 are contained within a lip of the protection sink. Also seen are reagent cartridges 210, which are shown disposed with thermal assemblies 211 which can create temperature zones appropriate for different reagents in different regions. Note that one of the reagent cartridges also comprises a flow-through electroporation device 230 (FTEP), served by FTEP interface (e.g., manifold arm) and actuator 231. Also seen is TFF module 222 with adjacent thermal assembly 225, where the TFF module is served by TFF interface (e.g., manifold arm) and actuator 223. Thermal assemblies 225, 235, and 245 encompass thermal electric devices such as Peltier devices, as well as heatsinks, fans and coolers. As in FIG. 2A, gantry 202, tip supply 214, cameras 239 and cooling grate 264 are seen.

The rotating growth vial 218 is within a growth module 234, where the growth module is served by two thermal assemblies 235. A selection module is seen at 220. Also seen is the SWIIN module 240, comprising a SWIIN cartridge 244, where the SWIIN module also comprises a thermal assembly 245, illumination 243 (in this embodiment, backlighting), evaporation and condensation control 249, and where the SWIIN module is served by SWIIN interface (e.g., manifold arm) and actuator 247. Also seen in this view is touch screen display 201, display actuator 203, illumination 205 (one on either side of multi-module cell processing instrument 200), and cameras 239 (one camera on either side of multi-module cell processing instrument 200). Finally, element 237 comprises electronics, such as a processor, circuit control boards, high-voltage amplifiers, power supplies, and power entry; as well as pneumatics, such as pumps, valves and sensors.

Figure 2C:
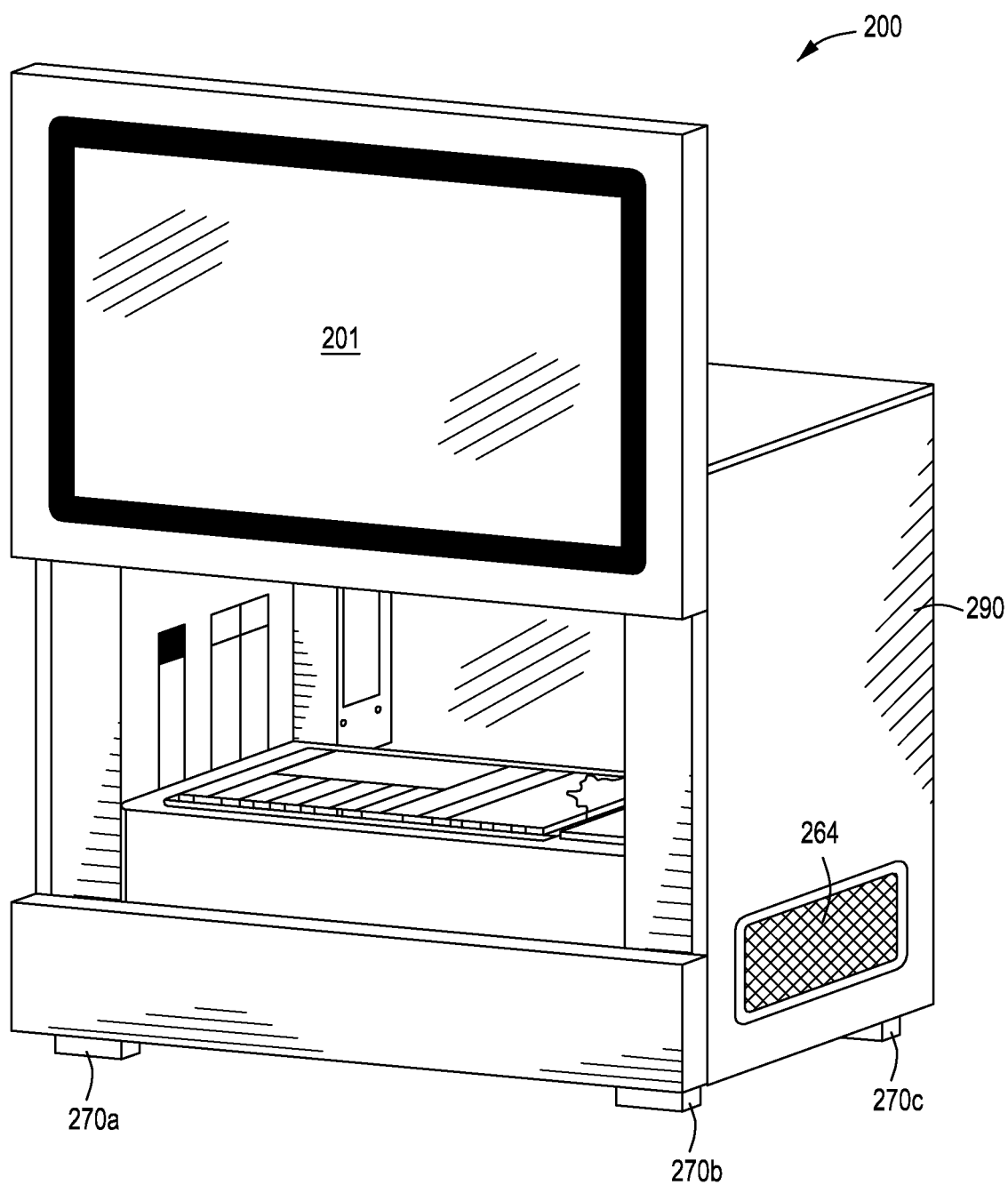

FIG. 2C illustrates a front perspective view of multi-module cell processing instrument 200 for use in as a benchtop version of the automated multi-module cell editing instrument 200. For example, a chassis 290 may have a width of about 24-48 inches, a height of about 24-48 inches and a depth of about 24-48 inches. Chassis 290 may be and preferably is designed to hold all modules and disposable supplies used in automated cell processing and to perform all processes required without human intervention; that is, chassis 290 is configured to provide an integrated, stand-alone automated multi-module cell processing instrument. As illustrated in FIG. 2C, chassis 290 includes touch screen display 201, cooling grate 264, which allows for air flow via an internal fan (not shown). The touch screen display provides information to a user regarding the processing status of the automated multi-module cell editing instrument 200 and accepts inputs from the user for conducting the cell processing. In this embodiment, the chassis 290 is lifted by adjustable feet 270a, 270b, 270c and 270d (feet 270a-270c are shown in this FIG. 2C). Adjustable feet 270a-270d, for example, allow for additional air flow beneath the chassis 290.

Inside the chassis 290, in some implementations, will be most or all of the components described in relation to FIGS. 2A and 2B, including the robotic liquid handling system disposed along a gantry, reagent cartridges 210 including a flow-through electroporation device, a rotating growth vial 218 in a cell growth module 234, a tangential flow filtration module 222, a SWIIN module 240 as well as interfaces and actuators for the various modules. In addition, chassis 290 houses control circuitry, liquid handling tubes, air pump controls, valves, sensors, thermal assemblies (e.g., heating and cooling units) and other control mechanisms. For examples of multi-module cell editing instruments, see U.S. Pat. Nos. 10,253,316; 10,329,559; 10,323,242; 10,421,959; 10,465,185; 10,519,437; 10,584,333; 10,584,334; 10,647, 982; 10,689,645; 10,738,301; 10,738,663; 10,947,532; 10,894,958; 10,954,512; and 11,034,953, all of which are herein incorporated by reference in their entirety.

Alternative Embodiment of an Automated Cell Editing Instrument

A bioreactor may be used to grow cells—in particular mammalian cells—off-instrument or to allow for cell growth and recovery on-instrument; e.g., as one module of a multi-module fully-automated closed instrument. Further, the bioreactor supports cell selection/enrichment, via expressed antibiotic markers in the growth process or via expressed antibodies coupled to magnetic beads and a magnet associated with the bioreactor. There are many bioreactors known in the art, including those described in, e.g., WO 2019/046766; 10,699,519; 10,633,625; 10,577,576; 10,294,447; 10,240,117; 10,179,898; 10,370,629; and 9,175,259; and those available from Lonza Group Ltd. (Basel, Switzerland); Miltenyi Biotec (Bergisch Gladbach, Germany), Terumo BCT (Lakewood, Colo.) and Sartorius GmbH (Gottingen, Germany).

Figure 3A:
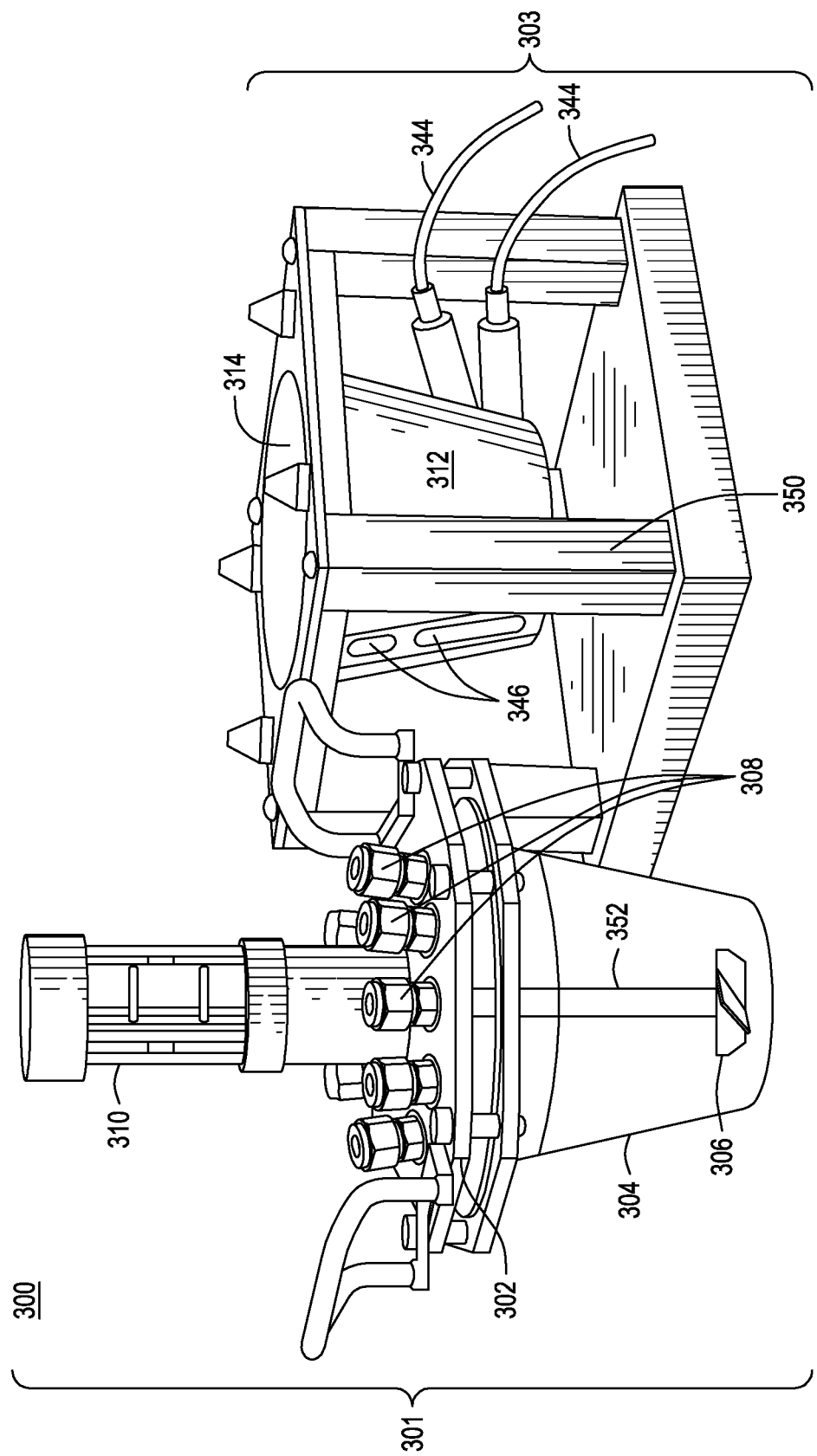
FIGS. 3A-3C depict various components of exemplary embodiments of a bioreactor module included in an integrated instrument useful for growing and transfecting cells.

FIG. 3A shows one embodiment of a bioreactor assembly 300 suitable for cell growth, transfection, and editing as one component of an automated multi-module cell processing instrument. Unlike most bioreactors that are used to support fermentation or other processes with an eye to harvesting the products produced by organisms grown in the bioreactor, the present bioreactor (and the processes performed therein) is configured to grow cells, monitor cell growth (via, e.g., optical means or capacitance), passage cells, select cells, transfect cells, and support the growth and harvesting of edited cells. Bioreactor assembly 300 comprises cell growth vessel 301 comprising a main body 304 with a lid assembly 302 comprising ports 308, including a motor integration port 310 configured to accommodate a motor to drive impeller 306 via impeller shaft 352. The tapered shape of main body 304 of the growth vessel 301 along with, in some embodiments, dual impellers allows for working with a larger dynamic range of volumes, such as, e.g., up to 500 ml and as low as 100 ml for rapid sedimentation of the microcarriers.

Bioreactor assembly 300 further comprises bioreactor stand assembly 303 comprising a main body 312 and growth vessel holder 314 comprising a heat jacket or other heating means (not shown) into which the main body 304 of growth vessel 301 is disposed in operation. The main body 304 of growth vessel 301 is biocompatible and preferably transparent—in some embodiments, in the UV and IR range as well as the visible spectrum—so that the growing cells can be visualized by, e.g., cameras or sensors integrated into lid assembly 302 or through viewing apertures or slots 346 in the main body 312 of bioreactor stand assembly 303. Camera mounts are shown at 344.

Bioreactor assembly 300 supports growth of cells from a 500,000 cell input to a 10 billion cell output, or from a 1 million cell input to a 25 billion cell output, or from a 5 million cell input to a 50 billion cell output or combinations of these ranges depending on, e.g., the size of main body 304 of growth vessel 301, the medium used to grow the cells, the type and size and number of microcarriers used for growth (if microcarriers are used), and whether the cells are adherent or non-adherent. The bioreactor that comprises assembly 300 supports growth of both adherent and non-adherent cells, wherein adherent cells are typically grown of microcarriers as described in detail in U.S. Ser. No. 17/237,747, filed 24 Apr. 2021. Alternatively, another option for growing mammalian cells in the bioreactor described herein is growing single cells in suspension using a specialized medium such as that developed by ACCELLTA™ (Haifa, Israel). Cells grown in this medium must be adapted to this process over many cell passages; however, once adapted the cells can be grown to a density of >40 million cells/ml and expanded 50-100× in approximately a week, depending on cell type.

Main body 304 of growth vessel 301 preferably is manufactured by injection molding, as is, in some embodiments, impeller 306 and the impeller shaft 352. Impeller 306 also may be fabricated from stainless steel, metal, plastics or the polymers listed infra. Injection molding allows for flexibility in size and configuration and also allows for, e.g., volume markings to be added to the main body 304 of growth vessel 301. Additionally, material from which the main body 304 of growth vessel 301 is fabricated should be able to be cooled to about 4° C. or lower and heated to about 55° C. or higher to accommodate cell growth. Further, the material that is used to fabricate the vial preferably is able to withstand temperatures up to 55° C. without deformation. Suitable materials for main body 304 of growth vessel 301 include cyclic olefin copolymer (COC), glass, polyvinyl chloride, polyethylene, polyetheretherketone (PEEK), polypropylene, polycarbonate, poly(methyl methacrylate (PMMA)), polysulfone, poly(dimethylsiloxane), cyclo-olefin polymer (COP), and co-polymers of these and other polymers. Preferred materials include polypropylene, polycarbonate, or polystyrene. The material used for fabrication may depend on the cell type to be grown, transfected and edited, and be conducive to growth of both adherent and non-adherent cells and workflows involving microcarrier-based transfection. The main body 304 of growth vessel 301 may be reusable or, alternatively, may be manufactured and configured for a single use. In one embodiment, main body 304 of growth vessel 301 may support cell culture volumes of 25 ml to 500 ml, but may be scaled up to support cell culture volumes of up to 3 L.

The bioreactor stand assembly comprises a stand or frame 350 and a main body 312 that holds the growth vessel 301 during operation. The stand/frame 350 and main body 312 are fabricated from stainless steel, other metals, or polymer/plastics. The bioreactor stand assembly main body further comprises a heat jacket (not seen in FIG. 3A) to maintain the growth vessel main body 304—and thus the cell culture—at a desired temperature. Additionally, the stand assembly can host a set of sensors and cameras (camera mounts are shown at 344) to monitor cell culture.

Figure 3B:
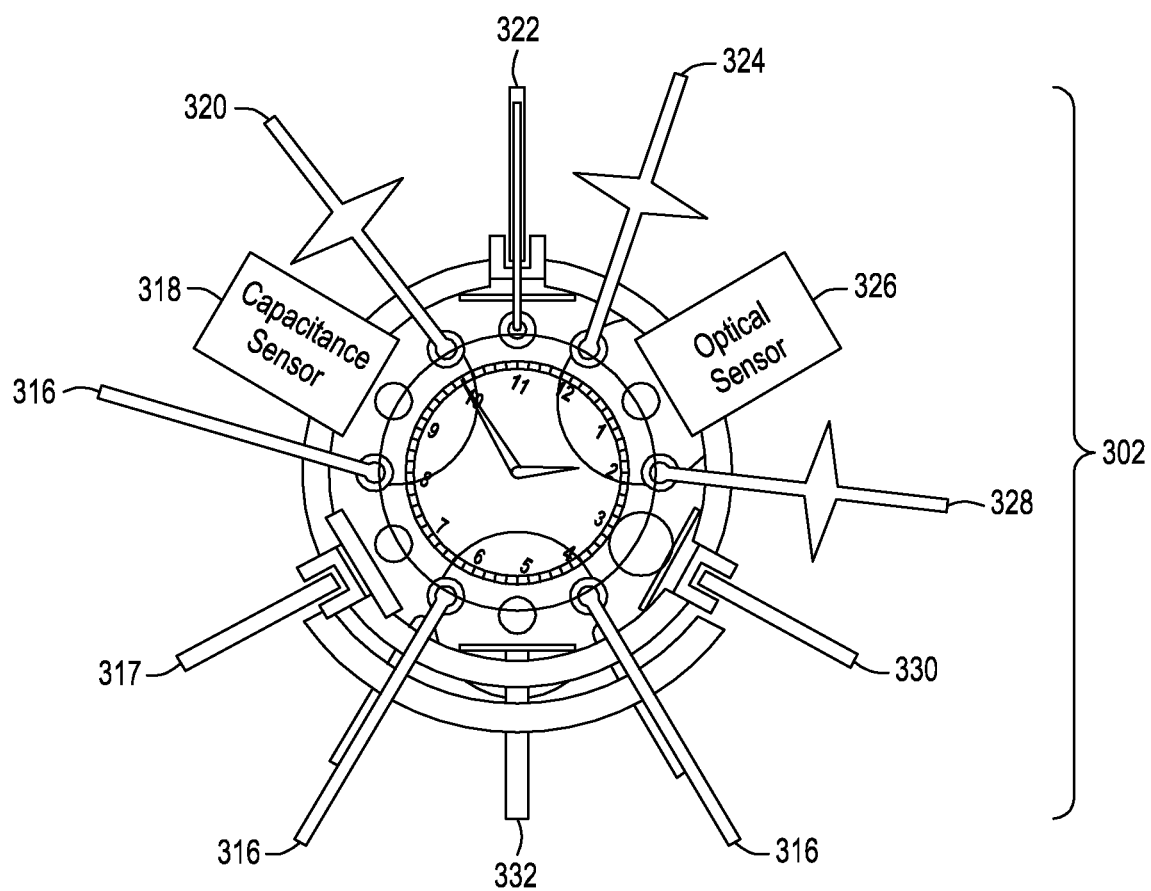

FIG. 3B depicts a top-down view of one embodiment of vessel lid assembly 302. Growth vessel lid assembly 302 is configured to be air-tight, providing a sealed, sterile environment for cell growth, transfection and editing as well as to provide biosafety in a closed system. Vessel lid assembly 302 and the main body of growth vessel can be reversibly sealed via fasteners such as screws, or permanently sealed using biocompatible glues or ultrasonic welding. Vessel lid assembly 302 in some embodiments is fabricated from stainless steel such as S316L stainless steel but may also be fabricated from metals, other polymers (such as those listed supra) or plastics. As seen in this FIG. 3B—as well as in FIG. 3A—vessel lid assembly 302 comprises a number of different ports to accommodate liquid addition and removal; gas addition and removal; for insertion of sensors to monitor culture parameters (described in more detail infra); to accommodate one or more cameras or other optical sensors; to provide access to the main body 304 of growth vessel 301 by, e.g., a liquid handling device; and to accommodate a motor for motor integration to drive one or more impellers 306. Exemplary ports depicted in FIG. 3B include three liquid-in ports 316 (at 4 o'clock, 6 o'clock and 8 o'clock); two self-sealing ports 317, 330 (at 3 o'clock and at 7 o'clock) to provide access to the main body 304 of growth vessel 301; one liquid-out port 322 (at 11 o'clock); a capacitance sensor 318 (at 9 o'clock); one "gas in" port 324 (at 12 o'clock); one "gas out" port 320 (at 10 o'clock); an optical sensor 326 (at 1 o'clock); a rupture disc 328 at 2 o'clock; and (a temperature probe 332 (at 5 o'clock).

The ports shown in vessel lid assembly 302 in this FIG. 3B are exemplary only and it should be apparent to one of ordinary skill in the art given the present disclosure that, e.g., a single liquid-in port 316 could be used to accommodate addition of all liquids to the cell culture rather than having a liquid-in port for each different liquid added to the cell culture. Further, any liquid-in port may serve as both a liquid-in port and a liquid-out port. Similarly, there may be more than one gas-in port 324, such as one for each gas, e.g., $O_2$, $CO_2$ that may be added. In addition, although a temperature probe 332 is shown, a temperature probe alternatively may be located on the outside of vessel holder 314 of bioreactor stand assembly 303 separate from or integrated into heater jacket (not seen in this FIG. 3B). A self-sealing port 330, if present, allows access to the main body 304 of growth vessel 301 for, e.g., a pipette, syringe, or other liquid delivery system via a gantry (not shown). As shown in FIG. 3A, additionally there may be a motor integration port 310 to drive the impeller(s), although other configurations of growth vessel 301 may alternatively integrate the motor drive at the bottom of the main body 304 of growth vessel 301. Growth vessel lid assembly 302 may also comprise a camera port for viewing and monitoring the cells.

Additional sensors include those that detect dissolved $O_2$ concentration, dissolved $CO_2$ concentration, culture pH, lactate concentration, glucose concentration, biomass, and optical density. The sensors may use optical (e.g., fluorescence detection), electrochemical, or capacitance sensing and either be reusable or configured and fabricated for single-use. Sensors appropriate for use in the bioreactor are available from Omega Engineering (Norwalk Conn.); PreSens Precision Sensing (Regensburg, Germany); C-CIT Sensors AG (Waedenswil, Switzerland), and ABER Instruments Ltd. (Alexandria, Va.). In one embodiment, optical density is measured using a reflective optical density sensor to facilitate sterilization, improve dynamic range and simplify mechanical assembly.

The rupture disc, if present, provides safety in a pressurized environment, and is programmed to rupture if a threshold pressure is exceeded in growth vessel. If the cell culture in the growth vessel is a culture of adherent cells, microcarriers may be used as described in U.S. Ser. No. 17/237,747, filed 24 Apr. 2021. In such an instance, the liquid-out port may comprise a filter such as a stainless steel or plastic (e.g., polyvinylidene difluoride (PVDF), nylon, polypropylene, polybutylene, acetal, polyethylene, or polyamide) filter or frit to prevent microcarriers from being drawn out of the culture during, e.g., medium exchange, but to allow dead cells to be withdrawn from the vessel. Additionally, a liquid port may comprise a filter sipper to allow cells that have been dissociated from microcarriers to be drawn into the cell corral while leaving spent microcarriers in main body 304 of growth vessel 301. The microcarriers used for initial cell growth can be nanoporous (where pore sizes are typically <20 nm in size), microporous (with pores between >20 nm to <1 μm in size), or macroporous (with pores between >1 μm in size, e.g. 20 μm) and the microcarriers are typically 50-200 μm in diameter; thus the pore size of the filter or frit in the liquid-out port will differ depending on microcarrier size.

The microcarriers used for cell growth depend on cell type and desired cell numbers, and typically include a coating of a natural or synthetic extracellular matrix or cell adhesion promoters (e.g., antibodies to cell surface proteins or poly-L-lysine) to promote cell growth and adherence. Microcarriers for cell culture are widely commercially available from, e.g., Millipore Sigma, (St. Louis, Mo., USA); ThermoFisher Scientific (Waltham, Mass., USA); Pall Corp. (Port Washington, N.Y., USA); GE Life Sciences (Marlborough, Mass., USA); and Corning Life Sciences (Tewkesbury, Mass., USA). As for the extracellular matrix, natural matrices include collagen, fibrin and vitronectin (available, e.g., from ESBio, Alameda, Calif., USA), and synthetic matrices include MATRIGEL® (Corning Life Sciences, Tewkesbury, Mass., USA), GELTREX™ (ThermoFisher Scientific, Waltham, Mass., USA), CULTREX® (Trevigen, Gaithersburg, Md., USA), biomemetic hydrogels available from Cellendes (Tubingen, Germany); and tissue-specific extracellular matrices available from Xylyx (Brooklyn, N.Y., USA); further, denovoMatrix (Dresden, Germany) offers screenMATRIX™, a tool that facilitates rapid testing of a large variety of cell microenvironments (e.g., extracellular matrices) for optimizing growth of the cells of interest.

Figure 3C:
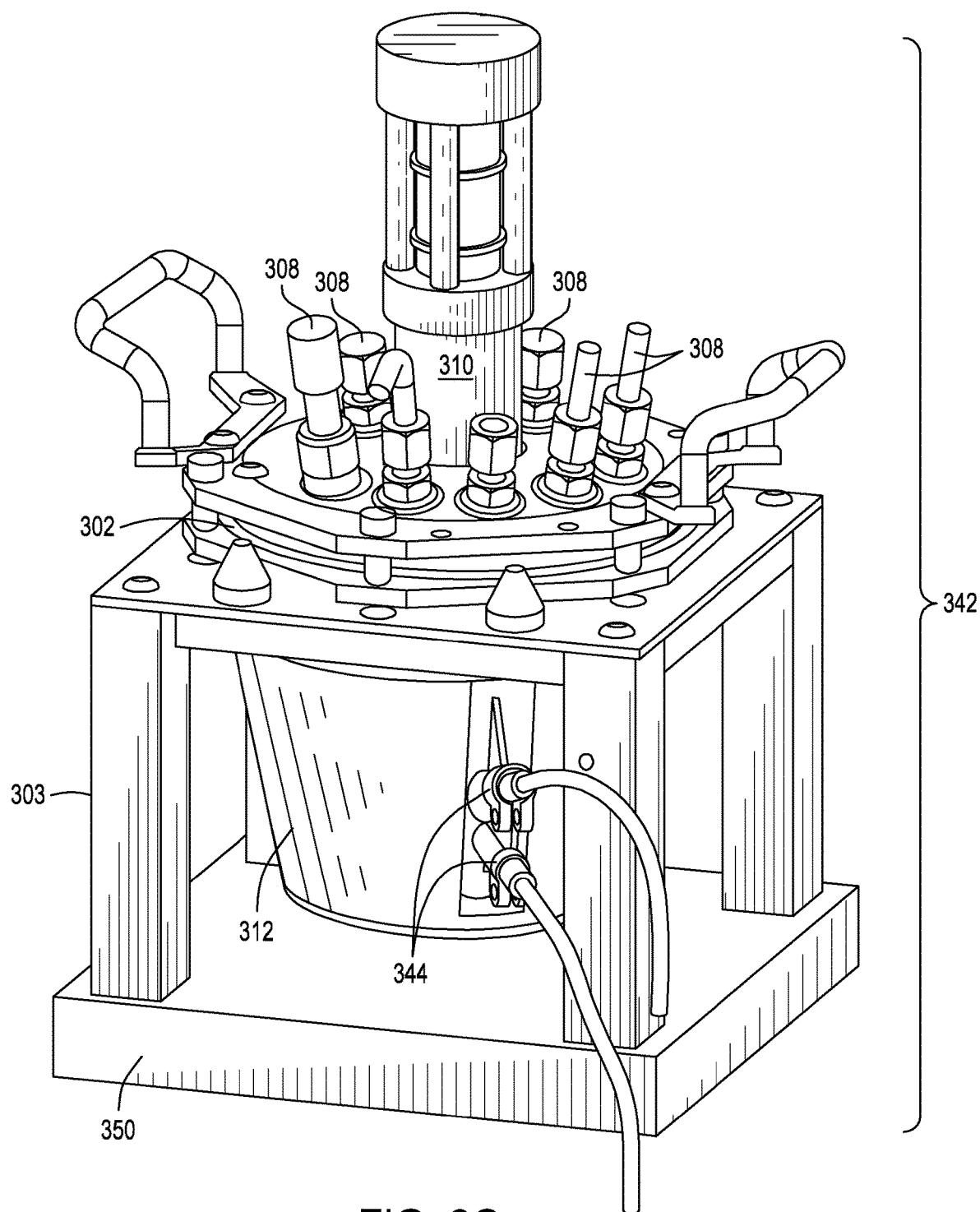

FIG. 3C is a side perspective view of the assembled bioreactor 342 without sensors mounted in ports 308. Seen are vessel lid assembly 302, bioreactor stand assembly 303, bioreactor stand main body 312 into which the main body of growth vessel 301 (not seen in this FIG. 3C) is inserted. Also present are two camera mounts 344, a motor integration port 310, and stand or frame 350.

Figure 3D:
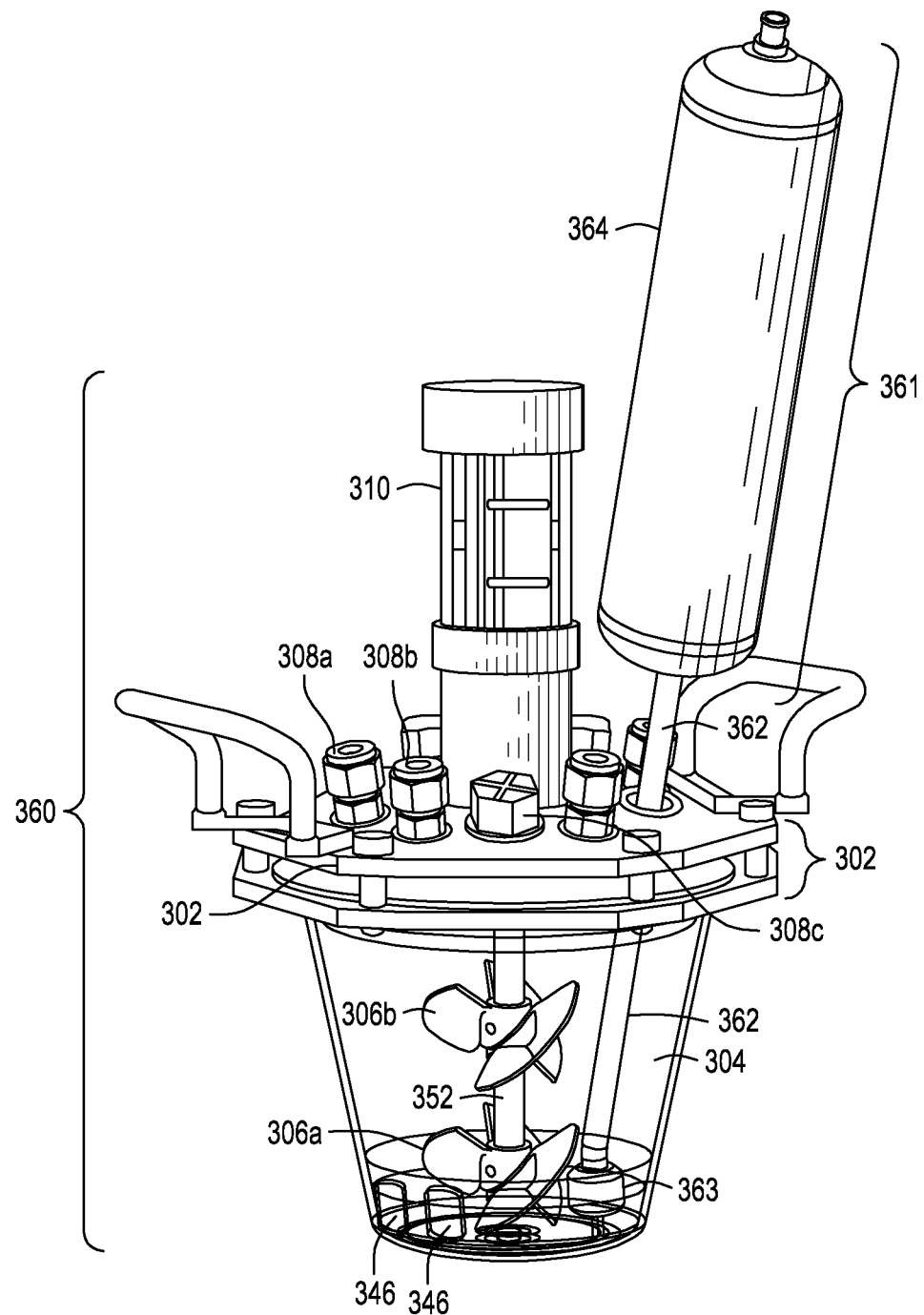
FIGS. 3D and 3E depict an exemplary integrated instrument for growing and transfecting cells.

FIG. 3D shows the embodiment of a bioreactor/cell corral assembly 360, comprising the bioreactor assembly 300 for cell growth, transfection, and editing described in FIG. 3A and further comprising a cell corral 361. Bioreactor assembly 300 comprises a growth vessel 301 (not labeled in this FIG. D) comprising tapered a main body 304 with a lid assembly 302 comprising ports 308 (here, 308a, 308b, 308c), including a motor integration port 310 driving impeller 306 via impeller shaft 352, as well as two viewing ports 346. Cell corral 361 comprises a main body 364, and end caps, where the end cap proximal the bioreactor assembly 300 is coupled to a filter sipper 362 comprising a filter portion 363 disposed within the main body 304 of the bioreactor assembly 300. The filter sipper is disposed within the main body 304 of the bioreactor assembly 300 but does not reach to the bottom surface of the bioreactor assembly 300 to leave a "dead volume" for spent microcarriers to settle while cells are removed from the growth vessel 301 into the cell corral 361. The cell corral may or may not comprise a temperature or $CO_2$ probe, and may or not be enclosed within an insulated jacket.

The cell corral 361, like the main body 304 of growth vessel 301 is fabricated from any biocompatible material such as polycarbonate, cyclic olefin copolymer (COC), glass, polyvinyl chloride, polyethylene, polyetheretherketone (PEEK), polypropylene, poly(methyl methacrylate (PMMA)), polysulfone, poly(dimethylsiloxane), cyclo-olefin polymer (COP), and co-polymers of these and other polymers. Likewise, the end caps of the cell corral are fabricated from a biocompatible material such as polycarbonate, cyclic olefin copolymer (COC), glass, polyvinyl chloride, polyethylene, polyetheretherketone (PEEK), polypropylene, poly(methyl methacrylate (PMMA)), polysulfone, poly(dimethylsiloxane), cyclo-olefin polymer (COP), and co-polymers of these and other polymers. The cell corral may be coupled to or integrated with one or more devices, such as a flow cell where an aliquot of the cell culture can be counted. Additionally, the cell corral may comprise additional liquid ports for adding medium, other reagents, and/or fresh microcarriers to the cells in the cell corral. The volume of the main body 364 of the cell corral 361 may be from 25 to 3000 mL, or from 250 to 1000 mL, or from 450 to 500 mL.

In operation, the bioreactor/cell corral assembly 360 comprising the bioreactor assembly 300 and cell corral 361 grows, passages, transfects, and supports editing and further growth of mammalian cells (note, the bioreactor stand assembly is not shown in this FIG. 3D). Cells are transferred to the growth vessel 301 comprising medium and microcarriers. The cells are allowed to adhere to the microcarries. Approximately 2000,000 microcarriers (e.g., laminin-521 coated polystyrene with enhanced attachment surface treatment) are used for the initial culture of approximately 20 million cells to where there are approximately 50 cells per microcarrier. The cells are grown until there are approximately 500 cells per microcarrier. For medium exchange, the microcarriers comprising the cells are allowed to settle and spent medium is aspirated via a sipper filter, wherein the filter has a mesh small enough to exclude the microcarriers. The mesh size of the filter will depend on the size of the microcarriers and cells present but typically is from 50 to 500 μm, or from 70 to 200 μm, or from 80 to 110 μm. For passaging the cells, the microcarriers are allowed to settle and spent medium is removed from the growth vessel 301, and phosphobuffered saline or another wash agent is added to the growth vessel 301 to wash the cells on the microcarriers. Optionally, the microcarriers are allowed to settle once again, and some of the wash agent is removed. At this point, the cells are dissociated from the microcarriers. Dissociation may be accomplished by, e.g., bubbling gas or air through the wash agent in the growth vessel 301, by increasing the impeller speed and/or direction, by enzymatic action (via, e.g., trypsin), or by a combination of these methods. In one embodiment, a chemical agent such as the RelesR™ reagent (STEMCELL Technologies Canada INC., Vancouver, BC) is added to the microcarriers in the remaining wash agent for a period of time required to dissociate most of the cells from the microcarriers, such as from 1 to 60 minutes, or from 3 to 25 minutes, or from 5 to 10 minutes. Once enough time has passed to dissociate the cells, cell growth medium is added to the growth vessel 301 to stop the enzymatic reaction.

Once again, the now-spent microcarriers are allowed to settle to the bottom of the growth vessel 301 and the cells are aspirated through a filter sipper into the cell corral 361. The growth vessel 301 is configured to allow for a "dead volume" of 2 mL to 200 mL, or 6 mL to 50 mL, or 8 mL to 12 mL below which the filter sipper does not aspirate medium to ensure the settled spent microcarriers are not transported to the filter sipper during fluid exchanges. Once the cells are aspirated from the bioreactor vessel leaving the "dead volume" of medium and spent microcarriers, the spent microcarriers are aspirated through a non-filter sipper into waste. The spent microcarriers (and the bioreactor vessel) are diluted in phosphobuffered saline or other buffer one or more times, wherein the wash agent and spent microcarriers continue to be aspirated via the non-filter sipper leaving a clean bioreactor vessel. After washing, fresh microcarriers or RBMCs and fresh medium are dispensed into the bioreactor vessel and the cells in the cell corral are dispensed back into the bioreactor vessel for another round of passaging or for transfection and editing, respectively.

Figure 3E:
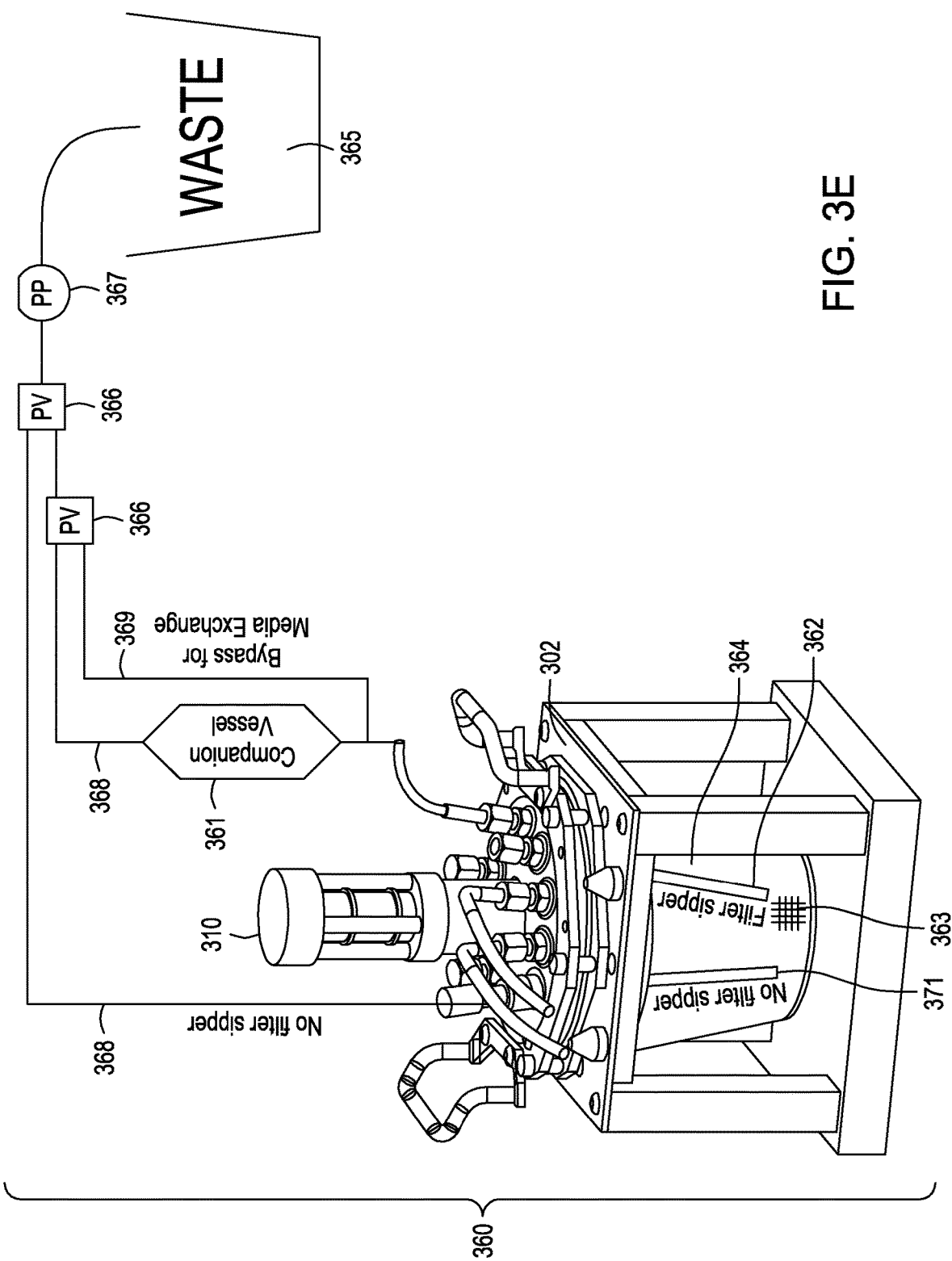

FIG. 3E depicts a bioreactor and bioreactor/cell corral assembly 360 comprising a growth vessel 301, with a main body 364, lid assembly 302 comprising a motor integration port 310, a filter sipper 362 comprising a filter 363 and a non-filter sipper 371, 368. Also seen is a cell corral 361, fluid line 368 from the cell corral through pinch valve 366, and a line 369 for medium exchange also connected to a pinch valve 366. The non-filter sipper 368 also runs through a pinch valve 366 to waste 365. Also seen is a peristaltic pump 367.

EXAMPLES

The following examples are put forth so as to provide those of ordinary skill in the art with a complete disclosure and description of how to make and use the present invention, and are not intended to limit the scope of what the inventors regard as their invention, nor are they intended to represent or imply that the experiments below are all of or the only experiments performed. It will be appreciated by persons skilled in the art that numerous variations and/or modifications may be made to the invention as shown in the specific aspects without departing from the spirit or scope of the invention as broadly described. The present aspects are, therefore, to be considered in all respects as illustrative and not restrictive.

Example I: Fully-Automated Singleplex RGN-Directed Editing Run

Singleplex automated genomic editing using MAD7 nuclease was successfully performed with an automated multi-module instrument of the disclosure. For examples of multi-module cell editing instruments, see U.S. Pat. No. 10,253,316, issued 9 Apr. 2019; U.S. Pat. No. 10,329,559, issued 25 Jun. 2019; U.S. Pat. No. 10,323,242, issued 18 Jun. 2019; U.S. Pat. No. 10,421,959, issued 24 Sep. 2019; U.S. Pat. No. 10,465,185, issued 5 Nov. 2019; U.S. Pat. No. 10,519,437, issued 31 Dec. 2019; U.S. Pat. No. 10,584,333, issued 10 Mar. 2020; U.S. Pat. No. 10,584,334, issued 10 Mar. 2020; U.S. Pat. No. 10,647,982, issued 12 May 2020; U.S. Pat. No. 10,689,645, issued 23 Jun. 2020; U.S. Pat. No. 10,738,301, issued 11 Aug. 2020; and U.S. Ser. No. 16/920,853, filed 6 Jul. 2020; and Ser. No. 16/988,694, filed 9 Aug. 2020, all of which are herein incorporated by reference in their entirety.

An ampR plasmid backbone and a lacZ_F172* editing cassette were assembled via Gibson Assembly® into an "editing vector" in an isothermal nucleic acid assembly module included in the automated instrument. lacZ_F172 functionally knocks out the lacZ gene. "lacZ_F172*" indicates that the edit happens at the 172nd residue in the lacZ amino acid sequence. Following assembly, the product was de-salted in the isothermal nucleic acid assembly module using AMPure beads, washed with 80% ethanol, and eluted in buffer. The assembled editing vector and recombineering-ready, electrocompetent E. Coli cells were transferred into a transformation module for electroporation. The cells and nucleic acids were combined and allowed to mix for 1 minute, and electroporation was performed for 30 seconds. The parameters for the poring pulse were: voltage, 2400 V; length, 5 ms; interval, 50 ms; number of pulses, 1; polarity, +. The parameters for the transfer pulses were: Voltage, 150 V; length, 50 ms; interval, 50 ms; number of pulses, 20; polarity, +/−. Following electroporation, the cells were transferred to a recovery module (another growth module), and allowed to recover in SOC medium containing chloramphenicol. Carbenicillin was added to the medium after 1 hour, and the cells were allowed to recover for another 2 hours. After recovery, the cells were held at 4° C. until recovered by the user.

After the automated process and recovery, an aliquot of cells was plated on MacConkey agar base supplemented with lactose (as the sugar substrate), chloramphenicol and carbenicillin and grown until colonies appeared. White colonies represented functionally edited cells, purple colonies represented un-edited cells. All liquid transfers were performed by the automated liquid handling device of the automated multi-module cell processing instrument.

The result of the automated processing was that approximately $1.0E^{0.3}$ total cells were transformed (comparable to conventional benchtop results), and the editing efficiency was 83.5%. The lacZ_172 edit in the white colonies was confirmed by sequencing of the edited region of the genome of the cells. Further, steps of the automated cell processing were observed remotely by webcam and text messages were sent to update the status of the automated processing procedure.

Example II: Fully-Automated Recursive Editing Run

Recursive editing was successfully achieved using the automated multi-module cell processing system. An ampR plasmid backbone and a lacZ_V10* editing cassette were assembled via Gibson Assembly® into an "editing vector" in an isothermal nucleic acid assembly module included in the automated system. Similar to the lacZ_F172 edit, the lacZ_V10 edit functionally knocks out the lacZ gene. "lacZ_V10" indicates that the edit happens at amino acid position 10 in the lacZ amino acid sequence. Following assembly, the product was de-salted in the isothermal nucleic acid assembly module using AMPure beads, washed with 80% ethanol, and eluted in buffer. The first assembled editing vector and the recombineering-ready electrocompetent E. coli cells were transferred into a transformation module for electroporation. The cells and nucleic acids were combined and allowed to mix for 1 minute, and electroporation was performed for 30 seconds. The parameters for the poring pulse were: voltage, 2400 V; length, 5 ms; interval, 50 ms; number of pulses, 1; polarity, +. The parameters for the transfer pulses were: Voltage, 150 V; length, 50 ms; interval, 50 ms; number of pulses, 20; polarity, +/−. Following electroporation, the cells were transferred to a recovery module (another growth module) allowed to recover in SOC medium containing chloramphenicol. Carbenicillin was added to the medium after 1 hour, and the cells were grown for another 2 hours. The cells were then transferred to a centrifuge module and a media exchange was then performed. Cells were resuspended in TB containing chloramphenicol and carbenicillin where the cells were grown to OD600 of 2.7, then concentrated and rendered electrocompetent.

During cell growth, a second editing vector was prepared in an isothermal nucleic acid assembly module. The second editing vector comprised a kanamycin resistance gene, and the editing cassette comprised a galK Y145* edit. If successful, the galK Y145* edit confers on the cells the ability to uptake and metabolize galactose. The edit generated by the galK Y145* cassette introduces a stop codon at the 154th amino acid reside, changing the tyrosine amino acid to a stop codon. This edit makes the galK gene product non-functional and inhibits the cells from being able to metabolize galactose. Following assembly, the second editing vector product was de-salted in the isothermal nucleic acid assembly module using AMPure beads, washed with 80% ethanol, and eluted in buffer. The assembled second editing vector and the electrocompetent E. coli cells (that were transformed with and selected for the first editing vector) were transferred into a transformation module for electroporation, using the same parameters as detailed above. Following electroporation, the cells were transferred to a recovery module (another growth module), allowed to recover in SOC medium containing carbenicillin. After recovery, the cells were held at 4° C. until retrieved, after which an aliquot of cells were plated on LB agar supplemented with chloramphenicol, and kanamycin. To quantify both lacZ and galK edits, replica patch plates were generated on two media types: 1) MacConkey agar base supplemented with lactose (as the sugar substrate), chloramphenicol, and kanamycin, and 2) MacConkey agar base supplemented with galactose (as the sugar substrate), chloramphenicol, and kanamycin. All liquid transfers were performed by the automated liquid handling device of the automated multi-module cell processing system.

In this recursive editing experiment, 41% of the colonies screened had both the lacZ and galK edits, the results of which were comparable to the double editing efficiencies obtained using a "benchtop" or manual approach.

While this invention is satisfied by embodiments in many different forms, as described in detail in connection with preferred embodiments of the invention, it is understood that the present disclosure is to be considered as exemplary of the principles of the invention and is not intended to limit the invention to the specific embodiments illustrated and described herein. Numerous variations may be made by persons skilled in the art without departure from the spirit of the invention. The scope of the invention will be measured by the appended claims and their equivalents. The abstract and the title are not to be construed as limiting the scope of the present invention, as their purpose is to enable the appropriate authorities, as well as the general public, to quickly determine the general nature of the invention. In the claims that follow, unless the term "means" is used, none of the features or elements recited therein should be construed as means-plus-function limitations pursuant to 35 U.S.C. § 112, ¶6.

I claim:

1. A method for multiplex insertion of large DNA payloads into a population of cells and identifying cells with a desired phenotype or genotype comprising the steps of:
   designing and synthesizing a library of editing cassettes comprising landing pads, wherein the editing cassettes further comprise a gRNA comprising homology to a target sequence in the cells and a repair template comprising 5' and 3' homology arms flanking the landing pad;
   inserting the library of editing cassettes into a vector backbone resulting in a library of editing vectors;
   transforming the population of cells with the library of editing vectors;
   allowing editing to take place in the population of cells to produce edited cells;
   transforming the edited cells with vectors carrying large DNA payloads, wherein the vectors carrying large DNA payloads further comprise a coding sequence for a recombinase or a meganuclease under control of an inducible promoter;
   inducing expression of the recombinase or meganuclease to insert the large DNA payloads into the landing pads; and
   screening for cells comprising the desired phenotype or genotype.

2. The method of claim 1, wherein the vectors carrying large DNA payloads comprise a coding sequence for a recombinase, the landing pads comprise a recognition sequence for the recombinase and the large DNA payloads comprise recognition sequences for the recombinase flanking the large DNA payload.

3. The method of claim 2, wherein the recombinase is a cyclization recombination enzyme (Cre) and the landing pad and large DNA payload comprise lox recombination sites.

4. The method of claim 2, wherein the recombinase is flippase and the landing pad and large DNA payload comprise flippase recognition targets (FRTs).

5. The method of claim 1, wherein the vectors carrying large DNA payloads comprise a coding sequence for a meganuclease, the landing pads comprise a recognition sequence for the meganuclease, and the large DNA payloads further comprise homologous recombination sequences flanking the DNA playloads.

6. The method of claim 5, wherein the meganuclease belongs to the LAGLIDADG family of nucleases.

7. The method of claim 6, wherein the meganuclease is I-SceI.

8. The method of claim 6, wherein the meganuclease is I-CreI.

9. The method of claim 6, wherein the meganuclease is I-DmoI.

10. The method of claim 1, wherein the editing cassettes further comprise a barcode.

11. The method of claim 1, wherein the editing cassettes further comprise an amplification priming site at the 3' end of the editing cassette.

12. The method of claim 1, wherein the vectors carrying the large DNA payloads further comprise a selectable marker and the method further comprises a selection step between the allowing step and the transforming the editing cells step.

13. The method of claim 12, wherein the selectable marker in the vectors carrying the large DNA payloads is different from a selectable marker in the editing cassettes.

14. The method of claim 1, wherein the vectors carrying the large DNA payloads comprise the coding sequence of the recombinase or meganuclease under the control of an inducible promoter.

15. The method of claim 14, wherein the inducible promoter is a pL promoter.

16. The method of claim 14, wherein the inducible promoter is a pBAD promoter.

17. The method of claim 1, wherein the vectors carrying large DNA payloads further comprise an origin of replication and a selectable marker.

18. The method of claim 1, wherein the large DNA payloads are from 100 bp to 100 Kb in length.

19. The method of claim 18, wherein the large DNA payloads are from 500 bp to 50 Kb in length.

20. The method of claim 1, wherein the screening step comprises polymerase chain reaction (PCR) analysis with appropriate primer sets; a metabolic test; measurement of transcript level; a phenotypic assay; detection of a protein product using an antibody specific to the protein product; or DNA sequencing of the integrated large DNA payload.

21. A method for multiplex insertion of large DNA payloads into a population of cells and identifying cells with a desired phenotype or genotype comprising the steps of:
   designing and synthesizing a library of editing cassettes comprising landing pads wherein the landing pads comprise a recognition sequence for a recombinase and wherein the editing cassettes further comprise a gRNA comprising homology to a target sequence in the cells and a repair template comprising 5' and 3' homology arms flanking the landing pad;
   inserting the library of editing cassettes into a vector backbone resulting in a library of editing vectors;
   transforming the population of cells with the library of editing vectors;

allowing editing to take place in the population of cells to produce edited cells;

transforming the edited cells with vectors carrying large DNA payloads, wherein the vectors carrying large DNA payloads further comprise a coding sequence for the recombinase under control of an inducible promoter;

inducing expression of the recombinase to insert the large DNA payloads into the landing pads; and screening for cells comprising the desired phenotype or genotype.

22. The method of claim 21, wherein the recombinase is a cyclization recombination enzyme (Cre) and the landing pad and large DNA payload comprise lox recombination sites.

23. The method of claim 21, wherein the recombinase is flippase and the landing pad and large DNA payload comprise flippase recognition targets (FRTs).

24. The method of claim 21, wherein the editing cassettes further comprise an amplification priming site at the 3' end of the editing cassette and wherein the vectors carrying the large DNA payloads further comprise a selectable marker and the method further comprises a selection step between the allowing step and the transforming the editing cells step.

25. A method for multiplex insertion of large DNA payloads into a population of cells and identifying cells with a desired phenotype or genotype comprising the steps of:

designing and synthesizing a library of editing cassettes comprising landing pads wherein the landing pads comprise a recognition sequence for a meganuclease and wherein the editing cassettes further comprise a gRNA comprising homology to a target sequence in the cells and a repair template comprising 5' and 3' homology arms flanking the landing pad;

inserting the library of editing cassettes into a vector backbone resulting in a library of editing vectors;

transforming the population of cells with the library of editing vectors;

allowing editing to take place in the population of cells to produce edited cells;

transforming the edited cells with vectors carrying large DNA payloads, wherein the vectors carrying large DNA payloads further comprise a coding sequence for the meganuclease under control of an inducible promoter;

inducing expression of the meganuclease to insert the large DNA payloads into the landing pads; and screening for cells comprising the desired phenotype or genotype.

26. The method of claim 25, wherein the meganuclease belongs to the LAGLIDADG family of nucleases.

27. The method of claim 26, wherein the meganuclease is I-SceI.

28. The method of claim 26, wherein the meganuclease is I-CreI.

29. The method of claim 26, wherein the meganuclease is I-DmoI.

30. The method of claim 25, wherein the editing cassettes further comprise an amplification priming site at the 3' end of the editing cassette and wherein the vectors carrying the large DNA payloads further comprise a selectable marker and the method further comprises a selection step between the allowing step and the transforming the editing cells step.

* * * * *

```
                          SEQUENCE LISTING

<160> NUMBER OF SEQ ID NOS: 1

<210> SEQ ID NO 1
<211> LENGTH: 9
<212> TYPE: PRT
<213> ORGANISM: Artificial Sequence
<220> FEATURE:
<223> OTHER INFORMATION: amino acid motif for nuclease family

<400> SEQUENCE: 1

Leu Ala Gly Leu Ile Asp Ala Asp Gly
1               5
```